US010238692B2

(12) United States Patent
Yang et al.

(10) Patent No.: US 10,238,692 B2
(45) Date of Patent: Mar. 26, 2019

(54) COMPOSITION COMPRISING A CULTURE SOLUTION OF MESENCHYMAL STEM CELLS FOR THE TREATMENT OF NEURAL DISEASES

(75) Inventors: Yoon-Sun Yang, Seoul (KR); Won Il Oh, Seoul (KR); Jong Wook Chang, Seoul (KR); Ju Yeon Kim, Seoul (KR)

(73) Assignee: MEDIPOST CO., LTD, Seoul (KR)

( * ) Notice: Subject to any disclaimer, the term of this patent is extended or adjusted under 35 U.S.C. 154(b) by 0 days.

(21) Appl. No.: 13/129,363

(22) PCT Filed: Nov. 16, 2009

(86) PCT No.: PCT/KR2009/006712
§ 371 (c)(1),
(2), (4) Date: Jun. 22, 2011

(87) PCT Pub. No.: WO2010/056075
PCT Pub. Date: May 20, 2010

(65) Prior Publication Data
US 2011/0262393 A1     Oct. 27, 2011

Related U.S. Application Data

(60) Provisional application No. 61/193,293, filed on Nov. 14, 2008.

(30) Foreign Application Priority Data

Nov. 14, 2008 (KR) .......... 10-2008-0113465
Aug. 5, 2009 (KR) .......... 10-2009-0072114
Nov. 11, 2009 (KR) .......... 10-2009-0108662

(51) Int. Cl.
| C12N 5/07 | (2010.01) |
| A61P 25/02 | (2006.01) |
| A61K 35/28 | (2015.01) |
| A61K 38/20 | (2006.01) |
| C12N 5/0793 | (2010.01) |
| C12N 5/0775 | (2010.01) |

(52) U.S. Cl.
CPC .......... *A61K 35/28* (2013.01); *A61K 38/2026* (2013.01); *C12N 5/0619* (2013.01); *C12N 5/0665* (2013.01); *C12N 2502/137* (2013.01); *C12N 2502/1358* (2013.01)

(58) Field of Classification Search
CPC combination set(s) only.
See application file for complete search history.

(56) References Cited

U.S. PATENT DOCUMENTS

| 5,733,542 A * | 3/1998 | Haynesworth et al. ..... 424/93.7 |
| 5,837,576 A | 11/1998 | Chen et al. |
| 6,372,494 B1 * | 4/2002 | Naughton et al. ............ 435/391 |
| 6,900,299 B1 | 5/2005 | Mohapatra et al. |
| 2004/0037775 A1 | 2/2004 | Siahaan et al. |
| 2004/0151701 A1 | 8/2004 | Kim et al. |
| 2004/0203142 A1 | 10/2004 | Rai |
| 2005/0239897 A1 * | 10/2005 | Pittenger ................ A61K 35/28 514/569 |
| 2007/0037200 A1 | 2/2007 | Ray et al. |
| 2007/0184038 A1 | 8/2007 | Tennekoon et al. |
| 2008/0013140 A1 | 1/2008 | Jeun |
| 2008/0131405 A1 * | 6/2008 | Jeun ....................... A61K 35/28 424/93.7 |
| 2008/0249157 A1 | 10/2008 | Cossio Mora et al. |
| 2009/0035321 A1 | 2/2009 | Springer et al. |
| 2009/0192105 A1 | 7/2009 | McSwiggen et al. |

FOREIGN PATENT DOCUMENTS

| EP | 1 302 534 A1 | 4/2003 |
| EP | 1 767 617 A1 | 3/2007 |
| KR | 10-2003-0069115 A | 8/2003 |
| KR | 10-2004-0016785 A | 2/2004 |
| WO | 2000/53019 A1 | 9/2000 |
| WO | 02/36751 A2 | 5/2002 |
| WO | 02/086108 A1 | 10/2002 |
| WO | 03/070922 A1 | 8/2003 |
| WO | 2005026343 A1 | 3/2005 |
| WO | 2007/084354 A2 | 7/2007 |
| WO | WO-2007/133030 A1 | 11/2007 |
| WO | 2010056075 A2 | 5/2010 |

OTHER PUBLICATIONS

Minguell et al., Biology and clinical utilization of mesenchymal progenitor cells, Brazilian J of Med and Biol Research, 33:881-887, 2000.*
Schindowski et al., Cell Tissue Res, 343:399-409, 2011.*
Ende et al., Journal of Medicine, 32(3&4): 241-247, 2001.*
Yang et al., Cytotherapy, 6(5):476-486, 2004.*
Yu et al., Immunology, 88:368-374, 1996.*
Nikolic et al., Stem Cells and Development 17:423-439, Mar. 26, 2008.*
Tsai et al., J Experimental Med., 204(6):1273-1280, May 21, 2007.*
Strelau et al., J Neuroscience, 20(23):8597-8603, 2000.*
Strelau et al., J Neural Transmission, 65 [Suppl]:197-203, 2003.*

(Continued)

*Primary Examiner* — Kimberly Ballard
*Assistant Examiner* — Stacey N MacFarlane
(74) *Attorney, Agent, or Firm* — Sughrue Mion, PLLC

(57) ABSTRACT

Provided are a pharmaceutical composition for prevention and treatment of a neural disease including at least one selected from the group consisting of mesenchymal stem cells (MSCs), a culture solution of the MSCs, activin A, PF4, decorin, galectin 3, GDF15, glypican 3, MFRP, ICAM5, IGFBP7, PDGF-AA, SPARCL1, thrombospondin-1, WISP1, progranulin, IL-4, a factor inducing expression thereof, and any combination thereof, and a method therefor.

13 Claims, 17 Drawing Sheets
(8 of 17 Drawing Sheet(s) Filed in Color)
Specification includes a Sequence Listing.

(56) References Cited

OTHER PUBLICATIONS

Susumu Ikehara, J of Hematotherapy and Stem Cell Research, 12:643-653, 2003.*
Weiss et al., Stem Cells, 24(3):781-792, Oct. 13, 2005.*
Smith et al., Journal of Neuroscience, 17(8): 2653-2657, 1997.*
Torrente and Polli, Cell Transplantation 17:1103-1113, Oct. 1, 2008.*
Sanberg et al., Ann. N.Y. Acad. Sci. 1049: 67-83 (2005).*
Kim et al., Stem Cells and Dev. 0(00): 2015.*
Laakso et al., Neurobiology of Aging, vol. 19, No. 1, pp. 23-31, 1998.*
Ende et al, Human umbilical cord blood cells ameliorate Alzheimer's disease in transgenic mice. J Med 32:241-247, 2001 [Abstract Only].*
El-Badri et al., Stem Cells and Dev, 15:497-506, 2006.*
Ende et al, Parkinson's disease mice and human umbilical cord blood, 33(1-4):173-80, 2002 [Abstract Only].*
Sanberg, Nature Reports Stem Cells, published online Oct. 11, 2007 Retrieved from <http://www.nature.com/stemcells/2007/0710/071011/full/stemcells.2007.98.html> Retrieved on Oct. 29, 2016.*
Hsieh et al., PLoS ONE, 8(8):e72604, Aug. 2013.*
Lijima-Ando, Kanae, et al., "Overexpression of Neprilysin Reduces Alzheimer Amyloid-β 3 42 (A β 42)-induced Neuron Loss and Intraneuronal A β 42 Deposits but Causes a Reduction in cAMP-responsive Element-binding Protein-mediated Transcription, Age-dependent Axon Pathology, and Premature Death in *Drosophila*," Journal of Biological Chemistry, Jul. 4, 2008, pp. 19066-19076, vol. 283, No. 27.
Bae, Jae-Sung, et al., "Bone Marrow-Derived Mesenchymal Stem Cells Promote Neuronal Networks with Functional Synaptic Transmission After Transplantation into Mice with Neurodegeneration," Stem Cells, 2007, pp. 1307-1316, vol. 25.
S. Maudsley, et al., "Protein twists and turns in Alzheimer disease," Nature Medicine, Apr. 2006, pp. 392-393, vol. 12, No. 4.
M. Mattson, "Pathways towards and away from Alzheimer's disease," Nature, Aug. 5, 2004, pp. 631-639, vol. 430.
D. Kondziolka, M.D., et al., "Transplantation of cultured human neuronal cells for patients with stroke," Neurology, 2000, pp. 565-569, vol. 55.
M. Pittenger, et al., "Multilineage Potential of Adult Human Mesenchymal Stem Cells," Science, 1999, pp. 143-147, vol. 284.
L. Campos, et al., "Definition of Optimal Conditions for Collection and Cryopreservation of Umbilical Cord Hematopoietic Cells," Cryobiology, 1995, pp. 511-515, vol. 32.
K. LeBlanc, et al., "HLA expression and immunologic properties of differentiated and undifferentiated mesenchymal stem cells," Experimental Hematology, 2003, pp. 890-896, vol. 31.
HM Lazarus, et al., "Ex vivo expansion and subsequent infusion of human bone marrow-derived stromal progenitor cells (mesenchymal progenitor cells): implications for therapeutic use," Bone Marrow Transplantation, 1995, pp. 557-564, vol. 16.
International Search Report dated Sep. 20, 2012 in PCT International Application No. PCT/KR2012/000788, filed Feb. 1, 2012.
C.J. Westmark, "What's hAPPening at synapses? the role of amyloid β-protein precursor and β-amyloid in neurological disorders," Molecular Psychiatry, 2013, vol. 18, pp. 425-434.
E. Blom et al., "Rapid Progression from Mild Cognitive Impairment to Alzheimer's Disease in Subjects with Elevated Levels of Tau in Cerebrospinal Fluid and the APOE ϵ4/ϵ4 Genotype," Dement Geriatr Cogn Discord, May 7, 2009, vol. 27, pp. 458-464.
G. Alves et al., "CSF amyloid-β and tau proteins, and cognitive performance, in early and untreated Parkinson's Disease: the Norwegian ParkWest study," J Neurol Neurosurg Psychiatry, 2010, vol. 81, pp. 1080-1086.
I. Mackenzie et al., "Senile plaques in temporal lobe epilepsy," Acta Neuropathol, 1994, vol. 87, pp. 504-510.
B. Klementiev et al., "A neural cell adhesion molecule-derived peptide reduces neuropathological signs and cognitive impairment induced by Abeta25-35," Neuroscience, 2007, vol. 145, pp. 209-224.
D. Simmons et al., "ICAM, an adhesion ligand of LFA-1, is homologous to the neural cell adhesion molecule NCAM," Nature, 1988, vol. 331, pp. 624-627.
International Search Report dated Aug. 9, 2010 in PCT International Application No. PCT/KR2009/006712, filed Nov. 16, 2009.
International Preliminary Report on Patentability dated May 17, 2011 in PCT International Application No. PCT/KR2009/006712, filed Nov. 16, 2009.
G. Bowman et al., "Alzheimer's disease and the blood-brain barrier: past, present and future," Aging Health, 2008, vol. 4(1), pp. 47-55.
International Written Opinion prepared by Hungarian Intellectual Patent Office dated Oct. 18, 2012 in Singaporean Application No. 201103411-3.
Second Office Action issued by the State Intellectual Property Office of the People's Republic of China on Feb. 5, 2013 in Chinese Application No. 200980154402.4.
Bantubungi et al., (2007) "Stem cell factor and mesenchymal and neural stem cell transplantation in a rat model of Huntington's Disease," Molecular and Cellular Neurosciences, 37(3): 454-470.
Cho Y H et al., (2006) "The behavioral effect of human mesenchymal stem cell transplantation in cold brain injured rats." Acta Neurochirurgica. Supplement, 99: 125-132.
Search Report dated Apr. 15, 2013 for European Patent Application No. 09 826 307.2.
N. Liu et al., "Protective Effect of Activin A to the Injury of PC12 Cells Induced by Paraquat," Chinese Journal of Clinical Neuroscience, vol. 14, No. 1, 2006, pp. 25-32.
E. Sadot et al., "Short- and long-term mechanisms of tau regulation in PC12 cells," Journal of Cell Science, vol. 108, 1995, pp. 2857-2864.
J. Zhou, et al., "The co-culture system of MSCs and injured PC12 in vitro could inhibit the apoptosis of PC12," Chin. J. Neurol, Jul. 2006, vol. 39, No. 7, pp. 481-484.
L. Yi-zhao, et al., "Autologous bone mesenchymal stem cell transplatation for Alzheimer's disease in 4 cases," Journal of Clinical Rehabilitative Tissue Engineering Research, Oct. 21, 2008, vol. 12, No. 43, pp. 8431-8433.
Zwart et al., (2008) "Analysis of neural potential of human umbilical cord blood-derived multipotent mesenchymal stem cells in response to a range of neurogenic stimuli," Journal of Neuroscience Research, 86: 1902-1915.
Zhou Jin, "Co-culture system of MSCs and A$\beta_{1-40}$ injured PC12 in vitro", a doctorial dissertation on Jan. 15, 2007, 72 pages.
The State Intellectual Property Office of the P.R.C. Communication dated Jan. 17, 2014, issued in corresponding Chinese Application No. 200980154402.4.
Canadian Office Action dated Nov. 25, 2013 issued in Canadian Patent Application No. 2,743,620.
Huang et al., "Effects of Co-grafts Mesenchymal Stem Cells and Nerve Growth Factor Suspension in the Repair of Spinal Cord Injury", Journal of Huazhong University of Science and Technology, 2006, vol. 26 (2), pp. 206-210.
Hou et al., "Induction of Umbilical Cord Blood Mesenchymal Stem Cells into Neuron-Like Cells In Vitro", International Journal of Hematology, 2003, vol. 78, pp. 256-261.
Moviglia et al., "Combined protocol of cell therapy for chronic spinal cord injury. Report on the electrical and functional recovery of two patients", Cytotherapy, 2006, vol. 8, 202-209.
Ende et al., "Parkinson's disease mice and human umbilical cord blood", J. Medicine, 2002, vol. 33, pp. 173-180.
Quinn et al., "Antioxidants in Alzheimer's disease-vitamin C delivery to a demanding brain", Journal of Alzheimer's Disease, 2003, vol. 5, pp. 309-313.
Sun, Miao-Kun, "Hypoxia, Ischemic Stroke, and Memory Deficits: Prospects for Therapy", IUBMB Life, 1999, vol. 48, pp. 373-378.
Azbill et al., "Impaired mitochondrial function, oxidative stress and altered antioxidant enzyme activities following traumatic spinal cord injury", Brain Research 1997, vol. 765, pp. 283-290.

(56) References Cited

OTHER PUBLICATIONS

Calza et al., "Neural stem cells and cholinergic neurons: Regulation by immunolesion and treatment with mitogens, retinoic acid, and nerve growth factor", PNAS, 2003, vol. 100, pp. 7325-7330.
Chen et al., "Intravenous Administration of Human Umbilical Cord Blood Reduces Behavioral Deficits After Stroke in Rats", Stroke, 2001, vol. 32, pp. 2682-2688.
Hamilton et al., "Insulin reduction of cerebral infarction due to transient focal ischemia", J. Neurosurgery, 1995, vol. 82, pp. 262-268.
Markesbery et al., "Oxidative Alterations in Neurodegenerative Diseases", Chapt. 2 in Pathogenesis of Neurodegenerative Diseases, Ed. M.P. Mattson, Humana Press Inc, Totowa, NJ, pp. 21-51.
Moroo et al., "Loss of insulin receptor immunoreactivity from the substantia nigra pars compacta neurons in Parkinson's disease", Acta Neuropathology, 1994, vol. 87, pp. 343-348.
Ji et al., "Interactions of Chemokines and Chemokine Receptors Mediate the Migration of Mesenchymal Stem Cells to the Impaired Site in the Brain After Hypoglossal Nerve Injury", Stem Cells, 2004, vol. 22, pp. 415-427.
Kurozumi et al., "Mesenchymal Stem Cells That Produce Neurotrophic Factors Reduce Ischemic Damage in the Rat Middle Cerebral Artery Occlusion Model", Molecular Therapy, 2005, vol. 11, pp. 96-104.
Tajbakhsh, S. "Stem cell: what's in a name?", Nature Reports Stem Cells, published online Jun. 25, 2009, pp. 1-5.
Alexanian, A.R. "Neural stem cells induce bone-marrow-derived mesenchymal stem cells to generate neural stem-like cells via juxtacrine and paracrine interactions", Experimental Cell Research 310 (2005): pp. 383-391.
Lou et al., "The effect of bone marrow stromal cells on neuronal differentiation of mesencephalic neural stem cells in Sprague-Dawley rats", Brain Research, 2003, 968(1), pp. 114-121.
Jang, YK., "Mesenchymal stem cells feeder layer from human umbilical cord blood for ex vivo expanded growth and proliferation of hematopoietic progenitor cells," Ann Hematol 85(5): 212-225, May 2006.
Kadereit, S., et al., Expansion of LTC-ICs and maintenance of p21 and BCL-2 expression in cord blood CD34(+)/CD38(−) early progenitors cultured over human MSCs as a feeder layer, Stem Cells 20(6): 573-582 (2002).
Lee, Oscar, "Isolation of multipotent mesenchymal stem cells from umbilical cord blood," Blood, Mar. 1, 2004, vol. 103, No. 5, pp. 1669-1675.
Jeong, J.A. et al., "Rapid neural differentiation of human cord blood-derived mesenchymal stem cells," Neuroreport, Aug. 6, 2004, vol. 15, No. 11, pp. 1731-1734.
Chen et al., "Therapeutic Benefit of Intracerebral Transplantation of Bone Marrow Stromal Cells After Cerebral Ischemia in Rats," Journal of the Neurological Sciences, 2001, vol. 189, pp. 49-57.
Rivera et al., "Mesenchymal Stem Cells Instruct Oligodendrogenic Fate Decision on Adult Neural Stem Cells", Stem Cells, 2006, vol. 24, No. 10, pp. 2209-2219, www.StemCells.com.
Indian Patent Office, Communication dated Jul. 4, 2017 by the Indian Patent Offce in copending Indian Patent Application No. 3607/DELNP/2011.
Pesheva et al., "Galectin-3 promotes neural cell adhesion and neurite growth", Journal of Neuroscience Research, 1998, vol. 54, p. 639-654 (Abstract).
Kuklinski et al., "Expression of galectin-3 in neuronally differentiating PC12 cells is regulated both via Ras/MAPK-dependent and -independent signalling pathways", Journal of Neurochemistry, 2003, vol. 87, p. 1112-1124.
Kupershmidt et al., "The neuroprotective effect of Activin A and B: implication for neurodegenerative diseases", Journal of Neurochemistry, 2007, vol. 103, p. 962-971.
Japan Patent Office, Communication dated Jul. 7, 2015, issued in corresponding Japanese Application No. 2014-129743.

* cited by examiner

SEQUENCE LISTING

<160> NUMBER OF SEQ ID NOS: 30

<210> SEQ ID NO 1
<211> LENGTH: 426
<212> TYPE: PRT
<213> ORGANISM: Homo sapiens

<400> SEQUENCE: 1

```
Met Pro Leu Leu Trp Leu Arg Gly Phe Leu Leu Ala Ser Cys Trp Ile
 1               5                  10                  15

Ile Val Arg Ser Ser Pro Thr Pro Gly Ser Glu Gly His Ser Ala Ala
                20                  25                  30

Pro Asp Cys Pro Ser Cys Ala Leu Ala Ala Leu Pro Lys Asp Val Pro
            35                  40                  45

Asn Ser Gln Pro Glu Met Val Glu Ala Val Lys Lys His Ile Leu Asn
        50                  55                  60

Met Leu His Leu Lys Lys Arg Pro Asp Val Thr Gln Pro Val Pro Lys
 65                 70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
               100                 105                 110

Met Asn Glu Leu Met Glu Gln Thr Ser Glu Ile Ile Thr Phe Ala Glu
           115                 120                 125

Ser Gly Thr Ala Arg Lys Thr Leu His Phe Glu Ile Ser Lys Glu Gly
       130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
    210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Glu Gly Glu Gly Lys Lys Lys
            260                 265                 270

Gly Gly Gly Glu Gly Gly Ala Gly Ala Asp Glu Glu Lys Glu Gln Ser
        275                 280                 285

His Arg Pro Phe Leu Met Leu Gln Ala Arg Gln Ser Glu Asp His Pro
    290                 295                 300

His Arg Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His Ala Asn Tyr Cys Glu Gly
```

```
              340             345             350
Glu Cys Pro Ser His Ile Ala Gly Thr Ser Gly Ser Ser Leu Ser Phe
            355                 360                 365

His Ser Thr Val Ile Asn His Tyr Arg Met Arg Gly His Ser Pro Phe
        370                 375                 380

Ala Asn Leu Lys Ser Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
                420                 425

<210> SEQ ID NO 2
<211> LENGTH: 101
<212> TYPE: PRT
<213> ORGANISM: Homo sapiens

<400> SEQUENCE: 2

Met Ser Ser Ala Ala Gly Phe Cys Ala Ser Arg Pro Gly Leu Leu Phe
1               5                   10                  15

Leu Gly Leu Leu Leu Leu Pro Leu Val Val Ala Phe Ala Ser Ala Glu
                20                  25                  30

Ala Glu Glu Asp Gly Asp Leu Gln Cys Leu Cys Val Lys Thr Thr Ser
            35                  40                  45

Gln Val Arg Pro Arg His Ile Thr Ser Leu Glu Val Ile Lys Ala Gly
        50                  55                  60

Pro His Cys Pro Thr Ala Gln Leu Ile Ala Thr Leu Lys Asn Gly Arg
65                  70                  75                  80

Lys Ile Cys Leu Asp Leu Gln Ala Pro Leu Tyr Lys Lys Ile Ile Lys
                85                  90                  95

Lys Leu Leu Glu Ser
            100

<210> SEQ ID NO 3
<211> LENGTH: 359
<212> TYPE: PRT
<213> ORGANISM: Homo sapiens

<400> SEQUENCE: 3

Met Lys Ala Thr Ile Ile Leu Leu Leu Ala Gln Val Ser Trp Ala
1               5                   10                  15

Gly Pro Phe Gln Gln Arg Gly Leu Phe Asp Phe Met Leu Glu Asp Glu
                20                  25                  30

Ala Ser Gly Ile Gly Pro Glu Val Pro Asp Asp Arg Asp Phe Glu Pro
            35                  40                  45

Ser Leu Gly Pro Val Cys Pro Phe Arg Cys Gln Cys His Leu Arg Val
        50                  55                  60

Val Gln Cys Ser Asp Leu Gly Leu Asp Lys Val Pro Lys Asp Leu Pro
65                  70                  75                  80

Pro Asp Thr Thr Leu Leu Asp Leu Gln Asn Asn Lys Ile Thr Glu Ile
                85                  90                  95

Lys Asp Gly Asp Phe Lys Asn Leu Lys Asn Leu His Ala Leu Ile Leu
            100                 105                 110

Val Asn Asn Lys Ile Ser Lys Val Ser Pro Gly Ala Phe Thr Pro Leu
        115                 120                 125

Val Lys Leu Glu Arg Leu Tyr Leu Ser Lys Asn Gln Leu Lys Glu Leu
```

```
                130             135             140
Pro Glu Lys Met Pro Lys Thr Leu Gln Glu Leu Arg Ala His Glu Asn
145                 150                 155                 160

Glu Ile Thr Lys Val Arg Lys Val Thr Phe Asn Gly Leu Asn Gln Met
                165                 170                 175

Ile Val Ile Glu Leu Gly Thr Asn Pro Leu Lys Ser Ser Gly Ile Glu
            180                 185                 190

Asn Gly Ala Phe Gln Gly Met Lys Lys Leu Ser Tyr Ile Arg Ile Ala
                195                 200                 205

Asp Thr Asn Ile Thr Ser Ile Pro Gln Gly Leu Pro Pro Ser Leu Thr
210                 215                 220

Glu Leu His Leu Asp Gly Asn Lys Ile Ser Arg Val Asp Ala Ala Ser
225                 230                 235                 240

Leu Lys Gly Leu Asn Asn Leu Ala Lys Leu Gly Leu Ser Phe Asn Ser
                245                 250                 255

Ile Ser Ala Val Asp Asn Gly Ser Leu Ala Asn Thr Pro His Leu Arg
                260                 265                 270

Glu Leu His Leu Asp Asn Asn Lys Leu Thr Arg Val Pro Gly Gly Leu
                275                 280                 285

Ala Glu His Lys Tyr Ile Gln Val Val Tyr Leu His Asn Asn Asn Ile
290                 295                 300

Ser Val Val Gly Ser Ser Asp Phe Cys Pro Pro Gly His Asn Thr Lys
305                 310                 315                 320

Lys Ala Ser Tyr Ser Gly Val Ser Leu Phe Ser Asn Pro Val Gln Tyr
                325                 330                 335

Trp Glu Ile Gln Pro Ser Thr Phe Arg Cys Val Tyr Val Arg Ser Ala
                340                 345                 350

Ile Gln Leu Gly Asn Tyr Lys
                355

<210> SEQ ID NO 4
<211> LENGTH: 97
<212> TYPE: PRT
<213> ORGANISM: Homo sapiens

<400> SEQUENCE: 4

Met Ala Asp Asn Phe Ser Val Ser Val Leu Cys Leu Phe Leu Pro Leu
1               5                   10                  15

Asp Gln Leu His Met Val Glu Gly Trp Gly Phe Cys Phe Tyr His Asp
                20                  25                  30

Phe Pro Phe Ser Leu Ser His Cys Val Ala Ser Pro Gly Leu Ile Cys
            35                  40                  45

Pro Met Arg Ala Cys Lys Leu Glu Pro Cys Ser Ser Ser Arg Phe
        50                  55                  60

Gly Lys Lys Ala Arg Gln Ser Glu Ala Trp Asp Ser Leu Thr Val Thr
65                  70                  75                  80

Leu Ser Pro Lys Gly Pro Gly Arg Lys Gly Val Asp Ser Ala Gly Arg
                85                  90                  95

Ser

<210> SEQ ID NO 5
<211> LENGTH: 308
<212> TYPE: PRT
<213> ORGANISM: Homo sapiens

<400> SEQUENCE: 5
```

```
Met Pro Gly Gln Glu Leu Arg Thr Val Asn Gly Ser Gln Met Leu Leu
 1               5                  10                  15

Val Leu Leu Val Leu Ser Trp Leu Pro His Gly Gly Ala Leu Ser Leu
             20                  25                  30

Ala Glu Ala Ser Arg Ala Ser Phe Pro Gly Pro Ser Glu Leu His Ser
         35                  40                  45

Glu Asp Ser Arg Phe Arg Glu Leu Arg Lys Arg Tyr Glu Asp Leu Leu
     50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                 85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305

<210> SEQ ID NO 6
<211> LENGTH: 580
<212> TYPE: PRT
<213> ORGANISM: Homo sapiens

<400> SEQUENCE: 6

Met Ala Gly Thr Val Arg Thr Ala Cys Leu Val Val Ala Met Leu Leu
 1               5                  10                  15

Ser Leu Asp Phe Pro Gly Gln Ala Gln Pro Pro Pro Pro Pro Pro Asp
             20                  25                  30

Ala Thr Cys His Gln Val Arg Ser Phe Phe Gln Arg Leu Gln Pro Gly
         35                  40                  45

Leu Lys Trp Val Pro Glu Thr Pro Val Pro Gly Ser Asp Leu Gln Val
```

```
                 50                  55                  60
    Cys Leu Pro Lys Gly Pro Thr Cys Cys Ser Arg Lys Met Glu Glu Lys
     65                  70                  75                  80

Tyr Gln Leu Thr Ala Arg Leu Asn Met Glu Gln Leu Leu Gln Ser Ala
                     85                  90                  95

Ser Met Glu Leu Lys Phe Leu Ile Ile Gln Asn Ala Ala Val Phe Gln
                    100                 105                 110

Glu Ala Phe Glu Ile Val Val Arg His Ala Lys Asn Tyr Thr Asn Ala
                    115                 120                 125

Met Phe Lys Asn Asn Tyr Pro Ser Leu Thr Pro Gln Ala Phe Glu Phe
                130                 135                 140

Val Gly Glu Phe Phe Thr Asp Val Ser Leu Tyr Ile Leu Gly Ser Asp
    145                 150                 155                 160

Ile Asn Val Asp Asp Met Val Asn Glu Leu Phe Asp Ser Leu Phe Pro
                    165                 170                 175

Val Ile Tyr Thr Gln Leu Met Asn Pro Gly Leu Pro Asp Ser Ala Leu
                    180                 185                 190

Asp Ile Asn Glu Cys Leu Arg Gly Ala Arg Arg Asp Leu Lys Val Phe
                195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
    225                 230                 235                 240

Asn Thr Thr Asp His Leu Lys Phe Ser Lys Asp Cys Gly Arg Met Leu
                    245                 250                 255

Thr Arg Met Trp Tyr Cys Ser Tyr Cys Gln Gly Leu Met Met Val Lys
                260                 265                 270

Pro Cys Gly Gly Tyr Cys Asn Val Val Met Gln Gly Cys Met Ala Gly
                275                 280                 285

Val Val Glu Ile Asp Lys Tyr Trp Arg Glu Tyr Ile Leu Ser Leu Glu
                290                 295                 300

Glu Leu Val Asn Gly Met Tyr Arg Ile Tyr Asp Met Glu Asn Val Leu
    305                 310                 315                 320

Leu Gly Leu Phe Ser Thr Ile His Asp Ser Ile Gln Tyr Val Gln Lys
                    325                 330                 335

Asn Ala Gly Lys Leu Thr Thr Thr Ile Gly Lys Leu Cys Ala His Ser
                340                 345                 350

Gln Gln Arg Gln Tyr Arg Ser Ala Tyr Tyr Pro Glu Asp Leu Phe Ile
                355                 360                 365

Asp Lys Lys Val Leu Lys Val Ala His Val Glu His Glu Glu Thr Leu
                370                 375                 380

Ser Ser Arg Arg Arg Glu Leu Ile Gln Lys Leu Lys Ser Phe Ile Ser
    385                 390                 395                 400

Phe Tyr Ser Ala Leu Pro Gly Tyr Ile Cys Ser His Ser Pro Val Ala
                    405                 410                 415

Glu Asn Asp Thr Leu Cys Trp Asn Gly Gln Glu Leu Val Glu Arg Tyr
                420                 425                 430

Ser Gln Lys Ala Ala Arg Asn Gly Met Lys Asn Gln Phe Asn Leu His
                435                 440                 445

Glu Leu Lys Met Lys Gly Pro Glu Pro Val Val Ser Gln Ile Ile Asp
                450                 455                 460

Lys Leu Lys His Ile Asn Gln Leu Leu Arg Thr Met Ser Met Pro Lys
    465                 470                 475                 480
```

Gly Arg Val Leu Asp Lys Asn Leu Asp Glu Glu Gly Phe Glu Ser Gly
            485                 490                 495

Asp Cys Gly Asp Glu Asp Glu Cys Ile Gly Gly Ser Gly Asp Gly
            500                 505                 510

Met Ile Lys Val Lys Asn Gln Leu Arg Phe Leu Ala Glu Leu Ala Tyr
            515                 520                 525

Asp Leu Asp Val Asp Ala Pro Gly Asn Ser Gln Gln Ala Thr Pro
            530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
            565                 570                 575

Phe Leu Val His
            580

<210> SEQ ID NO 7
<211> LENGTH: 579
<212> TYPE: PRT
<213> ORGANISM: Homo sapiens

<400> SEQUENCE: 7

Met Lys Asp Phe Ser Asp Val Ile Leu Cys Met Glu Ala Thr Glu Ser
1               5                   10                  15

Ser Lys Thr Glu Phe Cys Asn Pro Ala Phe Glu Pro Glu Ser Gly Pro
            20                  25                  30

Pro Cys Pro Pro Pro Val Phe Pro Glu Asp Ala Ser Tyr Ser Val Pro
        35                  40                  45

Ala Pro Trp His Gly Arg Arg Pro Arg Gly Leu Arg Pro Asp Cys Arg
    50                  55                  60

Phe Ser Trp Leu Cys Val Leu Leu Ser Ser Leu Leu Leu Leu Leu Leu
65                  70                  75                  80

Leu Gly Leu Leu Val Ala Ile Ile Leu Ala Gln Leu Gln Ala Ala Pro
                85                  90                  95

Pro Ser Gly Ala Ser His Ser Pro Leu Pro Ala Gly Gly Leu Thr Thr
            100                 105                 110

Thr Thr Thr Thr Pro Thr Ile Thr Thr Ser Gln Ala Ala Gly Thr Pro
        115                 120                 125

Lys Gly Gln Gln Glu Ser Gly Val Ser Pro Ser Pro Gln Ser Thr Cys
    130                 135                 140

Gly Gly Leu Leu Ser Gly Pro Arg Gly Phe Phe Ser Ser Pro Asn Tyr
145                 150                 155                 160

Pro Asp Pro Tyr Pro Pro Asn Thr His Cys Val Trp His Ile Gln Val
                165                 170                 175

Ala Thr Asp His Ala Ile Gln Leu Lys Ile Glu Ala Leu Ser Ile Glu
            180                 185                 190

Ser Val Ala Ser Cys Leu Phe Asp Arg Leu Glu Leu Ser Pro Glu Pro
        195                 200                 205

Glu Gly Pro Leu Leu Arg Val Cys Gly Arg Val Pro Pro Pro Thr Leu
    210                 215                 220

Asn Thr Asn Ala Ser His Leu Leu Val Val Phe Val Ser Asp Ser Ser
225                 230                 235                 240

Val Glu Gly Phe Gly Phe His Ala Trp Tyr Gln Ala Met Ala Pro Gly
                245                 250                 255

Arg Gly Ser Cys Ala His Asp Glu Phe Arg Cys Asp Gln Leu Ile Cys

```
                    260                 265                 270
Leu Leu Pro Asp Ser Val Cys Asp Gly Phe Ala Asn Cys Ala Asp Gly
            275                 280                 285

Ser Asp Glu Thr Asn Cys Ser Ala Lys Phe Ser Gly Cys Gly Gly Asn
        290                 295                 300

Leu Thr Gly Leu Gln Gly Thr Phe Ser Thr Pro Ser Tyr Leu Gln Gln
305                 310                 315                 320

Tyr Pro His Gln Leu Leu Cys Thr Trp His Ile Ser Val Pro Ala Gly
                325                 330                 335

His Ser Ile Glu Leu Gln Phe His Asn Phe Ser Leu Glu Ala Gln Asp
            340                 345                 350

Glu Cys Lys Phe Asp Tyr Val Glu Val Tyr Glu Thr Ser Ser Ser Gly
        355                 360                 365

Ala Phe Ser Leu Leu Gly Arg Phe Cys Gly Ala Glu Pro Pro Pro His
    370                 375                 380

Leu Val Ser Ser His His Glu Leu Ala Val Leu Phe Arg Thr Asp His
385                 390                 395                 400

Gly Ile Ser Ser Gly Gly Phe Ser Ala Thr Tyr Leu Ala Phe Asn Ala
                405                 410                 415

Thr Glu Asn Pro Cys Gly Pro Ser Glu Leu Ser Cys Gln Ala Gly Gly
            420                 425                 430

Cys Lys Gly Val Gln Trp Met Cys Asp Met Trp Arg Asp Cys Thr Asp
        435                 440                 445

Gly Ser Asp Asp Asn Cys Ser Gly Pro Leu Phe Pro Pro Glu Leu
    450                 455                 460

Ala Cys Glu Pro Val Gln Val Glu Met Cys Leu Gly Leu Ser Tyr Asn
465                 470                 475                 480

Thr Thr Ala Phe Pro Asn Ile Trp Val Gly Met Ile Thr Gln Glu Glu
                485                 490                 495

Val Val Glu Val Leu Ser Gly Tyr Lys Ser Leu Thr Ser Leu Pro Cys
            500                 505                 510

Tyr Gln His Phe Arg Arg Leu Leu Cys Gly Leu Leu Val Pro Arg Cys
        515                 520                 525

Thr Pro Leu Gly Ser Val Leu Pro Pro Cys Arg Ser Val Cys Gln Glu
    530                 535                 540

Ala Glu His Gln Cys Gln Ser Gly Leu Ala Leu Leu Gly Thr Pro Trp
545                 550                 555                 560

Pro Phe Asn Cys Asn Arg Leu Pro Glu Ala Ala Asp Leu Glu Ala Cys
                565                 570                 575

Ala Gln Pro

<210> SEQ ID NO 8
<211> LENGTH: 924
<212> TYPE: PRT
<213> ORGANISM: Homo sapiens

<400> SEQUENCE: 8

Met Pro Gly Pro Ser Pro Gly Leu Arg Arg Ala Leu Leu Gly Leu Trp
1               5                   10                  15

Ala Ala Leu Gly Leu Gly Leu Phe Gly Leu Ser Ala Val Ser Gln Glu
            20                  25                  30

Pro Phe Trp Ala Asp Leu Gln Pro Arg Val Ala Phe Val Glu Arg Gly
        35                  40                  45

Gly Ser Leu Trp Leu Asn Cys Ser Thr Asn Cys Pro Arg Pro Glu Arg
```

```
               50                  55                  60
Gly Gly Leu Glu Thr Ser Leu Arg Arg Asn Gly Thr Gln Arg Gly Leu
 65                  70                  75                  80

Arg Trp Leu Ala Arg Gln Leu Val Asp Ile Arg Pro Glu Thr Gln
                     85                  90                  95

Pro Val Cys Phe Phe Arg Cys Ala Arg Arg Thr Leu Gln Ala Arg Gly
                100                 105                 110

Leu Ile Arg Thr Phe Gln Arg Pro Asp Arg Val Glu Leu Met Pro Leu
                115                 120                 125

Pro Pro Trp Gln Pro Val Gly Glu Asn Phe Thr Leu Ser Cys Arg Val
130                 135                 140

Pro Gly Ala Gly Pro Arg Ala Ser Leu Thr Leu Thr Leu Leu Arg Gly
145                 150                 155                 160

Ala Gln Glu Leu Ile Arg Arg Ser Phe Ala Gly Glu Pro Pro Arg Ala
                165                 170                 175

Arg Gly Ala Val Leu Thr Ala Thr Val Leu Ala Arg Arg Glu Asp His
                180                 185                 190

Gly Ala Asn Phe Ser Cys Arg Ala Glu Leu Asp Leu Arg Pro His Gly
                195                 200                 205

Leu Gly Leu Phe Glu Asn Ser Ser Ala Pro Arg Glu Leu Arg Thr Phe
210                 215                 220

Ser Leu Ser Pro Asp Ala Pro Arg Leu Ala Ala Pro Arg Leu Leu Glu
225                 230                 235                 240

Val Gly Ser Glu Arg Pro Val Ser Cys Thr Leu Asp Gly Leu Phe Pro
                245                 250                 255

Ala Ser Glu Ala Arg Val Tyr Leu Ala Leu Gly Asp Gln Asn Leu Ser
                260                 265                 270

Pro Asp Val Thr Leu Glu Gly Asp Ala Phe Val Ala Thr Ala Thr Ala
                275                 280                 285

Thr Ala Ser Ala Glu Gln Glu Gly Ala Arg Gln Leu Val Cys Asn Val
290                 295                 300

Thr Leu Gly Gly Glu Asn Arg Glu Thr Arg Glu Asn Val Thr Ile Tyr
305                 310                 315                 320

Ser Phe Pro Ala Pro Leu Leu Thr Leu Ser Glu Pro Ser Val Ser Glu
                325                 330                 335

Gly Gln Met Val Thr Val Thr Cys Ala Ala Gly Ala Gln Ala Leu Val
                340                 345                 350

Thr Leu Glu Gly Val Pro Ala Ala Val Pro Gly Gln Pro Ala Gln Leu
                355                 360                 365

Gln Leu Asn Ala Thr Glu Asn Asp Asp Arg Arg Ser Phe Phe Cys Asp
                370                 375                 380

Ala Thr Leu Asp Val Asp Gly Glu Thr Leu Ile Lys Asn Arg Ser Ala
385                 390                 395                 400

Glu Leu Arg Val Leu Tyr Ala Pro Arg Leu Asp Asp Ser Asp Cys Pro
                405                 410                 415

Arg Ser Trp Thr Trp Pro Glu Gly Pro Glu Gln Thr Leu Arg Cys Glu
                420                 425                 430

Ala Arg Gly Asn Pro Glu Pro Ser Val His Cys Ala Arg Ser Asp Gly
                435                 440                 445

Gly Ala Val Leu Ala Leu Gly Leu Leu Gly Pro Val Thr Arg Ala Leu
                450                 455                 460

Ser Gly Thr Tyr Arg Cys Lys Ala Ala Asn Asp Gln Gly Glu Ala Val
465                 470                 475                 480
```

-continued

Lys Asp Val Thr Leu Thr Val Glu Tyr Ala Pro Ala Leu Asp Ser Val
            485                 490                 495
Gly Cys Pro Glu Arg Ile Thr Trp Leu Glu Gly Thr Glu Ala Ser Leu
                500                 505                 510
Ser Cys Val Ala His Gly Val Pro Pro Asp Val Ile Cys Val Arg
        515                 520                 525
Ser Gly Glu Leu Gly Ala Val Ile Glu Gly Leu Leu Arg Val Ala Arg
    530                 535                 540
Glu His Ala Gly Thr Tyr Arg Cys Glu Ala Thr Asn Pro Arg Gly Ser
545                 550                 555                 560
Ala Ala Lys Asn Val Ala Val Thr Val Glu Tyr Gly Pro Arg Phe Glu
                565                 570                 575
Glu Pro Ser Cys Pro Ser Asn Trp Thr Trp Val Glu Gly Ser Gly Arg
            580                 585                 590
Leu Phe Ser Cys Glu Val Asp Gly Lys Pro Gln Pro Ser Val Lys Cys
        595                 600                 605
Val Gly Ser Gly Gly Ala Thr Glu Gly Val Leu Leu Pro Leu Ala Pro
    610                 615                 620
Pro Asp Pro Ser Pro Arg Ala Pro Arg Ile Pro Arg Val Leu Ala Pro
625                 630                 635                 640
Gly Ile Tyr Val Cys Asn Ala Thr Asn Arg His Gly Ser Val Ala Lys
                645                 650                 655
Thr Val Val Ser Ala Glu Ser Pro Pro Glu Met Asp Glu Ser Thr
            660                 665                 670
Cys Pro Ser His Gln Thr Trp Leu Glu Gly Ala Glu Ala Ser Ala Leu
        675                 680                 685
Ala Cys Ala Ala Arg Gly Arg Pro Ser Pro Gly Val Arg Cys Ser Arg
    690                 695                 700
Glu Gly Ile Pro Trp Pro Glu Gln Gln Arg Val Ser Arg Glu Asp Ala
705                 710                 715                 720
Gly Thr Tyr His Cys Val Ala Thr Asn Ala His Gly Thr Asp Ser Arg
                725                 730                 735
Thr Val Thr Val Gly Val Glu Tyr Arg Pro Val Val Ala Glu Leu Ala
            740                 745                 750
Ala Ser Pro Pro Gly Gly Val Arg Pro Gly Gly Asn Phe Thr Leu Thr
        755                 760                 765
Cys Arg Ala Glu Ala Trp Pro Pro Ala Gln Ile Ser Trp Arg Ala Pro
    770                 775                 780
Pro Gly Ala Leu Asn Ile Gly Leu Ser Ser Asn Asn Ser Thr Leu Ser
785                 790                 795                 800
Val Ala Gly Ala Met Gly Ser His Gly Gly Glu Tyr Glu Cys Ala Ala
                805                 810                 815
Thr Asn Ala His Gly Arg His Ala Arg Arg Ile Thr Val Arg Val Ala
            820                 825                 830
Gly Pro Trp Leu Trp Val Ala Val Gly Gly Ala Ala Gly Gly Ala Ala
        835                 840                 845
Leu Leu Ala Ala Gly Ala Gly Leu Ala Phe Tyr Val Gln Ser Thr Ala
    850                 855                 860
Cys Lys Lys Gly Glu Tyr Asn Val Gln Glu Ala Glu Ser Ser Gly Glu
865                 870                 875                 880
Ala Val Cys Leu Asn Gly Ala Gly Gly Ala Gly Gly Ala Ala Gly
                885                 890                 895

```
Ala Glu Gly Gly Pro Glu Ala Ala Gly Ala Ala Glu Ser Pro Ala
            900                 905                 910

Glu Gly Glu Val Phe Ala Ile Gln Leu Thr Ser Ala
        915                 920

<210> SEQ ID NO 9
<211> LENGTH: 282
<212> TYPE: PRT
<213> ORGANISM: Homo sapiens

<400> SEQUENCE: 9

Met Glu Arg Pro Ser Leu Arg Ala Leu Leu Leu Gly Ala Ala Gly Leu
 1               5                  10                  15

Leu Leu Leu Leu Leu Pro Leu Ser Ser Ser Ser Ser Asp Thr Cys
                20                  25                  30

Gly Pro Cys Glu Pro Ala Ser Cys Pro Pro Leu Pro Pro Leu Gly Cys
             35                  40                  45

Leu Leu Gly Glu Thr Arg Asp Ala Cys Gly Cys Cys Pro Met Cys Ala
         50                  55                  60

Arg Gly Glu Gly Glu Pro Cys Gly Gly Gly Ala Gly Arg Gly Tyr
 65                  70                  75                  80

Cys Ala Pro Gly Met Glu Cys Val Lys Ser Arg Lys Arg Arg Lys Gly
                 85                  90                  95

Lys Ala Gly Ala Ala Ala Gly Gly Pro Gly Val Ser Gly Val Cys Val
            100                 105                 110

Cys Lys Ser Arg Tyr Pro Val Cys Gly Ser Asp Gly Thr Thr Tyr Pro
        115                 120                 125

Ser Gly Cys Gln Leu Arg Ala Ala Ser Gln Arg Ala Glu Ser Arg Gly
    130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu
        195                 200                 205

Leu Pro Gly Asp Arg Asp Asn Leu Ala Ile Gln Thr Arg Gly Gly Pro
    210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
            260                 265                 270

Pro Val Lys Lys Gly Glu Gly Ala Glu Leu
        275                 280

<210> SEQ ID NO 10
<211> LENGTH: 195
<212> TYPE: PRT
<213> ORGANISM: Homo sapiens

<400> SEQUENCE: 10

Met Arg Thr Leu Ala Cys Leu Leu Leu Leu Gly Cys Gly Tyr Leu Ala
 1               5                  10                  15
```

```
His Val Leu Ala Glu Ala Glu Ile Pro Arg Glu Val Ile Glu Arg
            20                  25                  30

Leu Ala Arg Ser Gln Ile His Ser Ile Arg Asp Leu Gln Arg Leu Leu
        35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Arg Ala Gln Gly Pro Pro Leu Pro Ser Ser Gln Gly Pro Ser Arg
        115                 120                 125

Val His His Arg Ser Val Lys Val Ala Lys Val Glu Tyr Val Arg Lys
    130                 135                 140

Lys Pro Lys Leu Lys Glu Val Gln Val Arg Leu Glu Glu His Leu Glu
145                 150                 155                 160

Cys Ala Cys Ala Thr Thr Ser Leu Asn Pro Asp Tyr Arg Glu Asp
                165                 170                 175

Thr Gly Arg Pro Arg Glu Ser Gly Lys Lys Arg Lys Arg Lys Arg Leu
            180                 185                 190

Lys Pro Thr
        195

<210> SEQ ID NO 11
<211> LENGTH: 664
<212> TYPE: PRT
<213> ORGANISM: Homo sapiens

<400> SEQUENCE: 11

Met Lys Thr Gly Leu Phe Phe Leu Cys Leu Leu Gly Thr Ala Ala Ala
1               5                   10                  15

Ile Pro Thr Asn Ala Arg Leu Leu Ser Asp His Ser Lys Pro Thr Ala
            20                  25                  30

Glu Thr Val Ala Pro Asp Asn Thr Ala Ile Pro Ser Leu Arg Ala Glu
        35                  40                  45

Ala Glu Glu Asn Glu Lys Glu Thr Ala Val Ser Thr Glu Asp Asp Ser
    50                  55                  60

His His Lys Ala Glu Lys Ser Ser Val Leu Ser Lys Glu Glu Ser
65                  70                  75                  80

His Glu Gln Ser Ala Glu Gln Gly Lys Ser Ser Ser Gln Glu Leu Gly
                85                  90                  95

Leu Lys Asp Gln Glu Asp Ser Asp Gly His Leu Ser Val Asn Leu Glu
            100                 105                 110

Tyr Ala Pro Thr Glu Gly Thr Leu Asp Ile Lys Glu Asp Met Ser Glu
        115                 120                 125

Pro Gln Glu Lys Lys Leu Ser Glu Asn Thr Asp Phe Leu Ala Pro Gly
    130                 135                 140

Val Ser Ser Phe Thr Asp Ser Asn Gln Gln Glu Ser Ile Thr Lys Arg
145                 150                 155                 160

Glu Glu Asn Gln Glu Gln Pro Arg Asn Tyr Ser His His Gln Leu Asn
                165                 170                 175

Arg Ser Ser Lys His Ser Gln Gly Leu Arg Asp Gln Gly Asn Gln Glu
            180                 185                 190
```

```
Gln Asp Pro Asn Ile Ser Asn Gly Glu Glu Glu Glu Lys Glu Pro
        195                 200                 205

Gly Glu Val Gly Thr His Asn Asp Asn Gln Glu Arg Lys Thr Glu Leu
    210                 215                 220

Pro Arg Glu His Ala Asn Ser Lys Gln Glu Glu Asp Asn Thr Gln Ser
225                 230                 235                 240

Asp Asp Ile Leu Glu Glu Ser Asp Gln Pro Thr Gln Val Ser Lys Met
            245                 250                 255

Gln Glu Asp Glu Phe Asp Gln Gly Asn Gln Glu Gln Glu Asp Asn Ser
        260                 265                 270

Asn Ala Glu Met Glu Glu Glu Asn Ala Ser Asn Val Asn Lys His Ile
            275                 280                 285

Gln Glu Thr Glu Trp Gln Ser Gln Glu Gly Lys Thr Gly Leu Glu Ala
        290                 295                 300

Ile Ser Asn His Lys Glu Thr Glu Glu Lys Thr Val Ser Glu Ala Leu
305                 310                 315                 320

Leu Met Glu Pro Thr Asp Asp Gly Asn Thr Thr Pro Arg Asn His Gly
            325                 330                 335

Val Asp Asp Asp Gly Asp Asp Asp Gly Asp Gly Thr Asp Gly
            340                 345                 350

Pro Arg His Ser Ala Ser Asp Asp Tyr Phe Ile Pro Ser Gln Ala Phe
            355                 360                 365

Leu Glu Ala Glu Arg Ala Gln Ser Ile Ala Tyr His Leu Lys Ile Glu
        370                 375                 380

Glu Gln Arg Glu Lys Val His Glu Asn Glu Asn Ile Gly Thr Thr Glu
385                 390                 395                 400

Pro Gly Glu His Gln Glu Ala Lys Lys Ala Glu Asn Ser Ser Asn Glu
            405                 410                 415

Glu Glu Thr Ser Ser Glu Gly Asn Met Arg Val His Ala Val Asp Ser
        420                 425                 430

Cys Met Ser Phe Gln Cys Lys Arg Gly His Ile Cys Lys Ala Asp Gln
            435                 440                 445

Gln Gly Lys Pro His Cys Val Cys Gln Asp Pro Val Thr Cys Pro Pro
        450                 455                 460

Thr Lys Pro Leu Asp Gln Val Cys Gly Thr Asp Asn Gln Thr Tyr Ala
465                 470                 475                 480

Ser Ser Cys His Leu Phe Ala Thr Lys Cys Arg Leu Glu Gly Thr Lys
            485                 490                 495

Lys Gly His Gln Leu Gln Leu Asp Tyr Phe Gly Ala Cys Lys Ser Ile
        500                 505                 510

Pro Thr Cys Thr Asp Phe Glu Val Ile Gln Phe Pro Leu Arg Met Arg
    515                 520                 525

Asp Trp Leu Lys Asn Ile Leu Met Gln Leu Tyr Glu Ala Asn Ser Glu
    530                 535                 540

His Ala Gly Tyr Leu Asn Glu Lys Gln Arg Asn Lys Val Lys Lys Ile
545                 550                 555                 560

Tyr Leu Asp Glu Lys Arg Leu Leu Ala Gly Asp His Pro Ile Asp Leu
            565                 570                 575

Leu Leu Arg Asp Phe Lys Lys Asn Tyr His Met Tyr Val Tyr Pro Val
        580                 585                 590

His Trp Gln Phe Ser Glu Leu Asp Gln His Pro Met Asp Arg Val Leu
    595                 600                 605
```

```
Thr His Ser Glu Leu Ala Pro Leu Arg Ala Ser Leu Val Pro Met Glu
    610                 615                 620

His Cys Ile Thr Arg Phe Phe Glu Glu Cys Asp Pro Asn Lys Asp Lys
625                 630                 635                 640

His Ile Thr Leu Lys Glu Trp Gly His Cys Phe Gly Ile Lys Glu Glu
                645                 650                 655

Asp Ile Asp Glu Asn Leu Leu Phe
            660

<210> SEQ ID NO 12
<211> LENGTH: 1170
<212> TYPE: PRT
<213> ORGANISM: Homo sapiens

<400> SEQUENCE: 12

Met Gly Leu Ala Trp Gly Leu Gly Val Leu Phe Leu Met His Val Cys
  1               5                  10                  15

Gly Thr Asn Arg Ile Pro Glu Ser Gly Gly Asp Asn Ser Val Phe Asp
                 20                  25                  30

Ile Phe Glu Leu Thr Gly Ala Ala Arg Lys Gly Ser Gly Arg Arg Leu
             35                  40                  45

Val Lys Gly Pro Asp Pro Ser Ser Pro Ala Phe Arg Ile Glu Asp Ala
 50                  55                  60

Asn Leu Ile Pro Pro Val Pro Asp Asp Lys Phe Gln Asp Leu Val Asp
 65                  70                  75                  80

Ala Val Arg Ala Glu Lys Gly Phe Leu Leu Leu Ala Ser Leu Arg Gln
                 85                  90                  95

Met Lys Lys Thr Arg Gly Thr Leu Leu Ala Leu Glu Arg Lys Asp His
            100                 105                 110

Ser Gly Gln Val Phe Ser Val Ser Asn Gly Lys Ala Gly Thr Leu
            115                 120                 125

Asp Leu Ser Leu Thr Val Gln Gly Lys Gln His Val Val Ser Val Glu
    130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
                165                 170                 175

Ala Glu Leu Asp Val Pro Ile Gln Ser Val Phe Thr Arg Asp Leu Ala
            180                 185                 190

Ser Ile Ala Arg Leu Arg Ile Ala Lys Gly Gly Val Asn Asp Asn Phe
        195                 200                 205

Gln Gly Val Leu Gln Asn Val Arg Phe Val Phe Gly Thr Thr Pro Glu
    210                 215                 220

Asp Ile Leu Arg Asn Lys Gly Cys Ser Ser Ser Thr Ser Val Leu Leu
225                 230                 235                 240

Thr Leu Asp Asn Asn Val Val Asn Gly Ser Ser Pro Ala Ile Arg Thr
                245                 250                 255

Asn Tyr Ile Gly His Lys Thr Lys Asp Leu Gln Ala Ile Cys Gly Ile
            260                 265                 270

Ser Cys Asp Glu Leu Ser Ser Met Val Leu Glu Leu Arg Gly Leu Arg
        275                 280                 285

Thr Ile Val Thr Thr Leu Gln Asp Ser Ile Arg Lys Val Thr Glu Glu
    290                 295                 300

Asn Lys Glu Leu Ala Asn Glu Leu Arg Arg Pro Pro Leu Cys Tyr His
305                 310                 315                 320
```

```
Asn Gly Val Gln Tyr Arg Asn Glu Glu Trp Thr Val Asp Ser Cys
                325                 330                 335

Thr Glu Cys His Cys Gln Asn Ser Val Thr Ile Cys Lys Lys Val Ser
            340                 345                 350

Cys Pro Ile Met Pro Cys Ser Asn Ala Thr Val Pro Asp Gly Glu Cys
                355                 360                 365

Cys Pro Arg Cys Trp Pro Ser Asp Ser Ala Asp Asp Gly Trp Ser Pro
            370                 375                 380

Trp Ser Glu Trp Thr Ser Cys Ser Thr Ser Cys Gly Asn Gly Ile Gln
385                 390                 395                 400

Gln Arg Gly Arg Ser Cys Asp Ser Leu Asn Asn Arg Cys Glu Gly Ser
                405                 410                 415

Ser Val Gln Thr Arg Thr Cys His Ile Gln Glu Cys Asp Lys Arg Phe
            420                 425                 430

Lys Gln Asp Gly Gly Trp Ser His Trp Ser Pro Trp Ser Ser Cys Ser
            435                 440                 445

Val Thr Cys Gly Asp Gly Val Ile Thr Arg Ile Arg Leu Cys Asn Ser
            450                 455                 460

Pro Ser Pro Gln Met Asn Gly Lys Pro Cys Glu Gly Glu Ala Arg Glu
465                 470                 475                 480

Thr Lys Ala Cys Lys Lys Asp Ala Cys Pro Ile Asn Gly Gly Trp Gly
                485                 490                 495

Pro Trp Ser Pro Trp Asp Ile Cys Ser Val Thr Cys Gly Gly Gly Val
                500                 505                 510

Gln Lys Arg Ser Arg Leu Cys Asn Asn Pro Thr Pro Gln Phe Gly Gly
                515                 520                 525

Lys Asp Cys Val Gly Asp Val Thr Glu Asn Gln Ile Cys Asn Lys Gln
530                 535                 540

Asp Cys Pro Ile Asp Gly Cys Leu Ser Asn Pro Cys Phe Ala Gly Val
545                 550                 555                 560

Lys Cys Thr Ser Tyr Pro Asp Gly Ser Trp Lys Cys Gly Ala Cys Pro
                565                 570                 575

Pro Gly Tyr Ser Gly Asn Gly Ile Gln Cys Thr Asp Val Asp Glu Cys
                580                 585                 590

Lys Glu Val Pro Asp Ala Cys Phe Asn His Asn Gly Glu His Arg Cys
                595                 600                 605

Glu Asn Thr Asp Pro Gly Tyr Asn Cys Leu Pro Cys Pro Pro Arg Phe
                610                 615                 620

Thr Gly Ser Gln Pro Phe Gly Gln Gly Val Glu His Ala Thr Ala Asn
625                 630                 635                 640

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
            660                 665                 670

Met Tyr Arg Cys Glu Cys Lys Pro Gly Tyr Ala Gly Asn Gly Ile Ile
            675                 680                 685

Cys Gly Glu Asp Thr Asp Leu Asp Gly Trp Pro Asn Glu Asn Leu Val
            690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
                725                 730                 735
```

```
Ala Cys Asp Asp Asp Asp Asn Asp Lys Ile Pro Asp Asp Arg Asp
            740                 745                 750

Asn Cys Pro Phe His Tyr Asn Pro Ala Gln Tyr Asp Tyr Asp Arg Asp
            755                 760                 765

Asp Val Gly Asp Arg Cys Asp Asn Cys Pro Tyr Asn His Asn Pro Asp
            770                 775                 780

Gln Ala Asp Thr Asp Asn Asn Gly Glu Gly Asp Ala Cys Ala Ala Asp
785                 790                 795                 800

Ile Asp Gly Asp Gly Ile Leu Asn Glu Arg Asp Asn Cys Gln Tyr Val
                805                 810                 815

Tyr Asn Val Asp Gln Arg Asp Thr Asp Met Asp Gly Val Gly Asp Gln
            820                 825                 830

Cys Asp Asn Cys Pro Leu Glu His Asn Pro Asp Gln Leu Asp Ser Asp
            835                 840                 845

Ser Asp Arg Ile Gly Asp Thr Cys Asp Asn Asn Gln Asp Ile Asp Glu
            850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
                885                 890                 895

Asp Asp Asp Asn Asp Gly Ile Pro Asp Asp Lys Asp Asn Cys Arg Leu
            900                 905                 910

Val Pro Asn Pro Asp Gln Lys Asp Ser Asp Gly Asp Gly Arg Gly Asp
            915                 920                 925

Ala Cys Lys Asp Asp Phe Asp His Asp Ser Val Pro Asp Ile Asp Asp
            930                 935                 940

Ile Cys Pro Glu Asn Val Asp Ile Ser Glu Thr Asp Phe Arg Arg Phe
945                 950                 955                 960

Gln Met Ile Pro Leu Asp Pro Lys Gly Thr Ser Gln Asn Asp Pro Asn
            965                 970                 975

Trp Val Val Arg His Gln Gly Lys Glu Leu Val Gln Thr Val Asn Cys
            980                 985                 990

Asp Pro Gly Leu Ala Val Gly Tyr Asp Glu Phe Asn Ala Val Asp Phe
            995                 1000                1005

Ser Gly Thr Phe Phe Ile Asn Thr Glu Arg Asp Asp Asp Tyr Ala Gly
    1010                1015                1020

Phe Val Phe Gly Tyr Gln Ser Ser Ser Arg Phe Tyr Val Val Met Trp
1025                1030                1035                1040

Lys Gln Val Thr Gln Ser Tyr Trp Asp Thr Asn Pro Thr Arg Ala Gln
            1045                1050                1055

Gly Tyr Ser Gly Leu Ser Val Lys Val Val Asn Ser Thr Thr Gly Pro
            1060                1065                1070

Gly Glu His Leu Arg Asn Ala Leu Trp His Thr Gly Asn Thr Pro Gly
            1075                1080                1085

Gln Val Arg Thr Leu Trp His Asp Pro Arg His Ile Gly Trp Lys Asp
            1090                1095                1100

Phe Thr Ala Tyr Arg Trp Arg Leu Ser His Arg Pro Lys Thr Gly Phe
1105                1110                1115                1120

Ile Arg Val Val Met Tyr Glu Gly Lys Lys Ile Met Ala Asp Ser Gly
                1125                1130                1135

Pro Ile Tyr Asp Lys Thr Tyr Ala Gly Gly Arg Leu Gly Leu Phe Val
            1140                1145                1150

Phe Ser Gln Glu Met Val Phe Phe Ser Asp Leu Lys Tyr Glu Cys Arg
```

Asp Pro
   1170

<210> SEQ ID NO 13
<211> LENGTH: 367
<212> TYPE: PRT
<213> ORGANISM: Homo sapiens

<400> SEQUENCE: 13

Met Arg Trp Phe Leu Pro Trp Thr Leu Ala Ala Val Thr Ala Ala Ala
 1               5                  10                  15

Ala Ser Thr Val Leu Ala Thr Ala Leu Ser Pro Ala Pro Thr Thr Met
            20                  25                  30

Asp Phe Thr Pro Ala Pro Leu Glu Asp Thr Ser Ser Arg Pro Gln Phe
        35                  40                  45

Cys Lys Trp Pro Cys Glu Cys Pro Pro Ser Pro Pro Arg Cys Pro Leu
    50                  55                  60

Gly Val Ser Leu Ile Thr Asp Gly Cys Glu Cys Cys Lys Met Cys Ala
65                  70                  75                  80

Gln Gln Leu Gly Asp Asn Cys Thr Glu Ala Ala Ile Cys Asp Pro His
                85                  90                  95

Arg Gly Leu Tyr Cys Asp Tyr Ser Gly Asp Arg Pro Arg Tyr Ala Ile
            100                 105                 110

Gly Val Cys Ala Gln Val Val Gly Val Gly Cys Val Leu Asp Gly Val
        115                 120                 125

Arg Tyr Asn Asn Gly Gln Ser Phe Gln Pro Asn Cys Lys Tyr Asn Cys
    130                 135                 140

Thr Cys Ile Asp Gly Ala Val Gly Cys Thr Pro Leu Cys Leu Arg Val
145                 150                 155                 160

Arg Pro Pro Arg Leu Trp Cys Pro His Pro Arg Arg Val Ser Ile Pro
                165                 170                 175

Gly His Cys Cys Glu Gln Trp Val Cys Glu Asp Asp Ala Lys Arg Pro
            180                 185                 190

Arg Lys Thr Ala Pro Arg Asp Thr Gly Ala Phe Asp Ala Val Gly Glu
        195                 200                 205

Val Glu Ala Trp His Arg Asn Cys Ile Ala Tyr Thr Ser Pro Trp Ser
    210                 215                 220

Pro Cys Ser Thr Ser Cys Gly Leu Gly Val Ser Thr Arg Ile Ser Asn
225                 230                 235                 240

Val Asn Ala Gln Cys Trp Pro Glu Gln Glu Ser Arg Leu Cys Asn Leu
                245                 250                 255

Arg Pro Cys Asp Val Asp Ile His Thr Leu Ile Lys Ala Gly Lys Lys
            260                 265                 270

Cys Leu Ala Val Tyr Gln Pro Glu Ala Ser Met Asn Phe Thr Leu Ala
        275                 280                 285

Gly Cys Ile Ser Thr Arg Ser Tyr Gln Pro Lys Tyr Cys Gly Val Cys
    290                 295                 300

Met Asp Asn Arg Cys Cys Ile Pro Tyr Lys Ser Lys Thr Ile Asp Val
305                 310                 315                 320

Ser Phe Gln Cys Pro Asp Gly Leu Gly Phe Ser Arg Gln Val Leu Trp
                325                 330                 335

Ile Asn Ala Cys Phe Cys Asn Leu Ser Cys Arg Asn Pro Asn Asp Ile
            340                 345                 350

Phe Ala Asp Leu Glu Ser Tyr Pro Asp Phe Ser Glu Ile Ala Asn
            355                 360                 365

<210> SEQ ID NO 14
<211> LENGTH: 438
<212> TYPE: PRT
<213> ORGANISM: Homo sapiens

<400> SEQUENCE: 14

Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
        275                 280                 285

Ser Cys Pro Asp Gly Tyr Thr Cys Cys Arg Leu Gln Ser Gly Ala Trp
    290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365

```
Val Ser Ser Cys Pro Ser Ser Asp Thr Cys Cys Arg Asp Asn Arg Gln
        370                 375                 380

Gly Trp Ala Cys Cys Pro Tyr Arg Gln Gly Val Cys Cys Ala Asp Arg
385                 390                 395                 400

Arg His Cys Cys Pro Ala Gly Phe Arg Cys Ala Ala Arg Gly Thr Lys
                405                 410                 415

Cys Leu Arg Arg Glu Ala Pro Arg Trp Asp Ala Pro Leu Arg Asp Pro
            420                 425                 430

Ala Leu Arg Gln Leu Leu
        435

<210> SEQ ID NO 15
<211> LENGTH: 21
<212> TYPE: DNA
<213> ORGANISM: Artificial Sequence
<220> FEATURE:
<223> OTHER INFORMATION: Forward primer for NEP gene amplification (rat)

<400> SEQUENCE: 15
tgctggagag agcaagcacg t                                           21

<210> SEQ ID NO 16
<211> LENGTH: 22
<212> TYPE: DNA
<213> ORGANISM: Artificial Sequence
<220> FEATURE:
<223> OTHER INFORMATION: Reverse primer for NEP gene amplification (rat)

<400> SEQUENCE: 16
atgagttgga ctgccgagca ct                                          22

<210> SEQ ID NO 17
<211> LENGTH: 20
<212> TYPE: DNA
<213> ORGANISM: Artificial Sequence
<220> FEATURE:
<223> OTHER INFORMATION: Forward primer for beta-actin gene
      amplification (human, mouse and rat)

<400> SEQUENCE: 17
tcctccctgg agaagagcta                                             20

<210> SEQ ID NO 18
<211> LENGTH: 22
<212> TYPE: DNA
<213> ORGANISM: Artificial Sequence
<220> FEATURE:
<223> OTHER INFORMATION: reverse primer for beta-actin gene
      amplification (human, mouse and rat)

<400> SEQUENCE: 18
aggaggagca atgatcttga tc                                          22

<210> SEQ ID NO 19
<211> LENGTH: 770
<212> TYPE: PRT
<213> ORGANISM: Homo sapiens

<400> SEQUENCE: 19

Met Leu Pro Gly Leu Ala Leu Leu Leu Ala Ala Trp Thr Ala Arg
  1               5                  10                  15

Ala Leu Glu Val Pro Thr Asp Gly Asn Ala Gly Leu Leu Ala Glu Pro
            20                  25                  30
```

```
Gln Ile Ala Met Phe Cys Gly Arg Leu Asn Met His Met Asn Val Gln
         35                  40                  45

Asn Gly Lys Trp Asp Ser Asp Pro Ser Gly Thr Lys Thr Cys Ile Asp
 50                  55                  60

Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
                 85                  90                  95

Trp Cys Lys Arg Gly Arg Lys Gln Cys Lys Thr His Pro His Phe Val
                100                 105                 110

Ile Pro Tyr Arg Cys Leu Val Gly Glu Phe Val Ser Asp Ala Leu Leu
                115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
                180                 185                 190

Ser Asp Asn Val Asp Ser Ala Asp Ala Glu Glu Asp Asp Ser Asp Val
                195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
                260                 265                 270

Ala Thr Thr Thr Thr Thr Thr Glu Ser Val Glu Glu Val Val Arg
                275                 280                 285

Glu Val Cys Ser Glu Gln Ala Glu Thr Gly Pro Cys Arg Ala Met Ile
290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
                340                 345                 350

Thr Gln Glu Pro Leu Ala Arg Asp Pro Val Lys Leu Pro Thr Thr Ala
                355                 360                 365

Ala Ser Thr Pro Asp Ala Val Asp Lys Tyr Leu Glu Thr Pro Gly Asp
                370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
                420                 425                 430

Gln His Phe Gln Glu Lys Val Glu Ser Leu Glu Gln Glu Ala Ala Asn
                435                 440                 445
```

```
Glu Arg Gln Gln Leu Val Glu Thr His Met Ala Arg Val Glu Ala Met
    450                 455                 460

Leu Asn Asp Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770

<210> SEQ ID NO 20
<211> LENGTH: 441
<212> TYPE: PRT
<213> ORGANISM: Homo sapiens

<400> SEQUENCE: 20

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45
```

```
Gln Thr Pro Thr Glu Asp Gly Ser Glu Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Ala Lys Gly
130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
            435                 440

<210> SEQ ID NO 21
<211> LENGTH: 750
```

<212> TYPE: PRT
<213> ORGANISM: Homo sapiens

<400> SEQUENCE: 21

```
Met Gly Lys Ser Glu Ser Gln Met Asp Ile Thr Asp Ile Asn Thr Pro
  1               5                  10                  15

Lys Pro Lys Lys Lys Gln Arg Trp Thr Pro Leu Glu Ile Ser Leu Ser
             20                  25                  30

Val Leu Val Leu Leu Leu Thr Ile Ile Ala Val Thr Met Ile Ala Leu
         35                  40                  45

Tyr Ala Thr Tyr Asp Asp Gly Ile Cys Lys Ser Ser Asp Cys Ile Lys
     50                  55                  60

Ser Ala Ala Arg Leu Ile Gln Asn Met Asp Ala Thr Thr Glu Pro Cys
 65                  70                  75                  80

Thr Asp Phe Phe Lys Tyr Ala Cys Gly Gly Trp Leu Lys Arg Asn Val
                 85                  90                  95

Ile Pro Glu Thr Ser Ser Arg Tyr Gly Asn Phe Asp Ile Leu Arg Asp
            100                 105                 110

Glu Leu Glu Val Val Leu Lys Asp Val Leu Gln Glu Pro Lys Thr Glu
        115                 120                 125

Asp Ile Val Ala Val Gln Lys Ala Lys Ala Leu Tyr Arg Ser Cys Ile
    130                 135                 140

Asn Glu Ser Ala Ile Asp Ser Arg Gly Gly Glu Pro Leu Leu Lys Leu
145                 150                 155                 160

Leu Pro Asp Ile Tyr Gly Trp Pro Val Ala Thr Glu Asn Trp Glu Gln
                165                 170                 175

Lys Tyr Gly Ala Ser Trp Thr Ala Glu Lys Ala Ile Ala Gln Leu Asn
            180                 185                 190

Ser Lys Tyr Gly Lys Lys Val Leu Ile Asn Leu Phe Val Gly Thr Asp
        195                 200                 205

Asp Lys Asn Ser Val Asn His Val Ile His Ile Asp Gln Pro Arg Leu
    210                 215                 220

Gly Leu Pro Ser Arg Asp Tyr Tyr Glu Cys Thr Gly Ile Tyr Lys Glu
225                 230                 235                 240

Ala Cys Thr Ala Tyr Val Asp Phe Met Ile Ser Val Ala Arg Leu Ile
                245                 250                 255

Arg Gln Glu Glu Arg Leu Pro Ile Asp Glu Asn Gln Leu Ala Leu Glu
            260                 265                 270

Met Asn Lys Val Met Glu Leu Glu Lys Glu Ile Ala Asn Ala Thr Ala
        275                 280                 285

Lys Pro Glu Asp Arg Asn Asp Pro Met Leu Leu Tyr Asn Lys Met Thr
    290                 295                 300

Leu Ala Gln Ile Gln Asn Phe Ser Leu Glu Ile Asn Gly Lys Pro
305                 310                 315                 320

Phe Ser Trp Leu Asn Phe Thr Asn Glu Ile Met Ser Thr Val Asn Ile
                325                 330                 335

Ser Ile Thr Asn Glu Glu Asp Val Val Val Tyr Ala Pro Glu Tyr Leu
            340                 345                 350

Thr Lys Leu Lys Pro Ile Leu Thr Lys Tyr Ser Ala Arg Asp Leu Gln
        355                 360                 365

Asn Leu Met Ser Trp Arg Phe Ile Met Asp Leu Val Ser Ser Leu Ser
    370                 375                 380

Arg Thr Tyr Lys Glu Ser Arg Asn Ala Phe Arg Lys Ala Leu Tyr Gly
385                 390                 395                 400
```

```
Thr Thr Ser Glu Thr Ala Thr Trp Arg Arg Cys Ala Asn Tyr Val Asn
            405                 410                 415

Gly Asn Met Glu Asn Ala Val Gly Arg Leu Tyr Val Glu Ala Ala Phe
            420                 425                 430

Ala Gly Glu Ser Lys His Val Val Glu Asp Leu Ile Ala Gln Ile Arg
            435                 440                 445

Glu Val Phe Ile Gln Thr Leu Asp Asp Leu Thr Trp Met Asp Ala Glu
            450                 455                 460

Thr Lys Lys Arg Ala Glu Glu Lys Ala Leu Ala Ile Lys Glu Arg Ile
465                 470                 475                 480

Gly Tyr Pro Asp Asp Ile Val Ser Asn Asp Asn Lys Leu Asn Asn Glu
            485                 490                 495

Tyr Leu Glu Leu Asn Tyr Lys Gly Asp Glu Tyr Phe Glu Asn Ile Ile
            500                 505                 510

Gln Asn Leu Lys Phe Ser Gln Ser Lys Gln Leu Lys Lys Leu Arg Glu
            515                 520                 525

Lys Val Asp Lys Asp Glu Trp Ile Ser Gly Ala Ala Val Val Asn Ala
            530                 535                 540

Phe Tyr Ser Ser Gly Arg Asn Gln Ile Val Phe Pro Ala Gly Ile Leu
545                 550                 555                 560

Gln Pro Pro Phe Phe Ser Ala Gln Gln Ser Asn Ser Leu Asn Tyr Gly
            565                 570                 575

Gly Ile Gly Met Val Ile Gly His Glu Ile Thr His Gly Phe Asp Asp
            580                 585                 590

Asn Gly Arg Asn Phe Asn Lys Asp Gly Asp Leu Val Asp Trp Trp Thr
            595                 600                 605

Gln Gln Ser Ala Ser Asn Phe Lys Glu Gln Ser Gln Cys Met Val Tyr
            610                 615                 620

Gln Tyr Gly Asn Phe Ser Trp Asp Leu Ala Gly Gly Gln His Leu Asn
625                 630                 635                 640

Gly Ile Asn Thr Leu Gly Glu Asn Ile Ala Asp Asn Gly Gly Leu Gly
            645                 650                 655

Gln Ala Tyr Arg Ala Tyr Gln Asn Tyr Ile Lys Lys Asn Gly Glu Glu
            660                 665                 670

Lys Leu Leu Pro Gly Leu Asp Leu Asn His Lys Gln Leu Phe Phe Leu
            675                 680                 685

Asn Phe Ala Gln Val Trp Cys Gly Thr Tyr Arg Pro Glu Tyr Ala Val
            690                 695                 700

Asn Ser Ile Lys Thr Asp Val His Ser Pro Gly Asn Phe Arg Ile Ile
705                 710                 715                 720

Gly Thr Leu Gln Asn Ser Ala Glu Phe Ser Glu Ala Phe His Cys Arg
            725                 730                 735

Lys Asn Ser Tyr Met Asn Pro Glu Lys Lys Cys Arg Val Trp
            740                 745                 750

<210> SEQ ID NO 22
<211> LENGTH: 20
<212> TYPE: DNA
<213> ORGANISM: Artificial Sequence
<220> FEATURE:
<223> OTHER INFORMATION: forward primer for IL-4

<400> SEQUENCE: 22
actgcttccc cctctgttct                                           20
```

```
<210> SEQ ID NO 23
<211> LENGTH: 20
<212> TYPE: DNA
<213> ORGANISM: Artificial Sequence
<220> FEATURE:
<223> OTHER INFORMATION: reverse primer for IL-4

<400> SEQUENCE: 23
agtgtccttc tcatggtggc                                                 20

<210> SEQ ID NO 24
<211> LENGTH: 20
<212> TYPE: DNA
<213> ORGANISM: Artificial Sequence
<220> FEATURE:
<223> OTHER INFORMATION: forward primer for IL-6

<400> SEQUENCE: 24
agttcctgca gaaaaaggca                                                 20

<210> SEQ ID NO 25
<211> LENGTH: 20
<212> TYPE: DNA
<213> ORGANISM: Artificial Sequence
<220> FEATURE:
<223> OTHER INFORMATION: reverse primer for IL-6

<400> SEQUENCE: 25
aacaacaatc tgaggtgccc                                                 20

<210> SEQ ID NO 26
<211> LENGTH: 22
<212> TYPE: DNA
<213> ORGANISM: Artificial Sequence
<220> FEATURE:
<223> OTHER INFORMATION: forward primer for IL-8

<400> SEQUENCE: 26
tcctgatttc tgcagctctg tg                                              22

<210> SEQ ID NO 27
<211> LENGTH: 22
<212> TYPE: DNA
<213> ORGANISM: Artificial Sequence
<220> FEATURE:
<223> OTHER INFORMATION: reverse primer for IL-8

<400> SEQUENCE: 27
tgcttgaagt ttcactggca tc                                              22

<210> SEQ ID NO 28
<211> LENGTH: 20
<212> TYPE: DNA
<213> ORGANISM: Artificial Sequence
<220> FEATURE:
<223> OTHER INFORMATION: forward primer for MCP-1 (CCL2)

<400> SEQUENCE: 28
ccccagtcac ctgctgttat                                                 20

<210> SEQ ID NO 29
<211> LENGTH: 20
<212> TYPE: DNA
<213> ORGANISM: Artificial Sequence
<220> FEATURE:
<223> OTHER INFORMATION: reverse primer for MCP-1 (CCL2)
```

```
<400> SEQUENCE: 29
agatctcctt ggccacaatg                                           20

<210> SEQ ID NO 30
<211> LENGTH: 153
<212> TYPE: PRT
<213> ORGANISM: Homo sapiens

<400> SEQUENCE: 30

Met Gly Leu Thr Ser Gln Leu Leu Pro Pro Leu Phe Phe Leu Leu Ala
 1               5                  10                  15

Cys Ala Gly Asn Phe Val His Gly His Lys Cys Asp Ile Thr Leu Gln
                20                  25                  30

Glu Ile Ile Lys Thr Leu Asn Ser Leu Thr Glu Gln Lys Thr Leu Cys
            35                  40                  45

Thr Glu Leu Thr Val Thr Asp Ile Phe Ala Ala Ser Lys Asn Thr Thr
        50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
                100                 105                 110

Asn Leu Trp Gly Leu Ala Gly Leu Asn Ser Cys Pro Val Lys Glu Ala
            115                 120                 125

Asn Gln Ser Thr Leu Glu Asn Phe Leu Glu Arg Leu Lys Thr Ile Met
        130                 135                 140

Arg Glu Lys Tyr Ser Lys Cys Ser Ser
145                 150
```

COMPOSITION COMPRISING A CULTURE SOLUTION OF MESENCHYMAL STEM CELLS FOR THE TREATMENT OF NEURAL DISEASES

CROSS REFERENCE TO RELATED APPLICATION

This application is a National Stage of International Application No. PCT/KR2009/006712 filed Nov. 16, 2009, claiming priority based on U.S. Provisional Patent Application No. 61/193,293, filed Nov. 14, 2008 and Korean Patent Application Nos. 10-2008-0113465 filed Nov. 14, 2008, 10-2009-0072114 filed Aug. 5, 2009 and 10-2009-0108662 filed Nov. 11, 2009, the contents of all of which are incorporated herein by reference in their entirety.

TECHNICAL FIELD

The present invention relates to a composition including mesenchymal stem cells (MSCs), a culture solution of MSCs, proteins contained in a culture solution of MSCs, or a signal transduction system-stimulating factor inducing expression of the proteins for the prevention or treatment of Alzheimer's disease, related to damage of neurites.

The present invention relates to a composition including mesenchymal stem cells (MSCs), a culture solution of MSCs, proteins contained in a culture solution of MSCs, or a signal transduction system-stimulating factor inducing expression of the proteins, for the prevention or treatment of a disease related to damage of neurites.

BACKGROUND ART

Alzheimer's disease, which is a brain disorder that destroys brain cells by a destructive accumulation of amyloid-beta protein and generally outbreaks with aging, is a serious disease resulting in speech impediment and recognition disorder. Alzheimer's disease proceeds in stages and gradually destroys memory, reasoning, judgment, language, and the ability to carry out even simple tasks. Eventually, loss of emotional control may cause degradation of human life. Currently, Alzheimer's disease cannot be completely cured, but drugs relieving symptoms are clinically applied. However, effects of these drugs on patients are limited. Around half of Alzheimer's disease patients fail to be cured from initial drug treatment. Even if the initial drug treatment is successful, only a slight alleviation of symptoms is experienced. Thus, there is a need to develop a novel treatment for satisfying medical demands, and the development of a treatment for Alzheimer's disease will have large economical and social effects. It is known that as Alzheimer's disease proceeds, the cerebral cortex and hippocampus are destroyed and cannot be restored, and thus there is no treatment therefor.

Research on Alzheimer's disease has been driven by a focus on two proteins, tau and amyloid precursor protein (APP) (Stuart M. and Mark P. M, Nature Medicine, 12(4), 392-393, 2006). Brains of affected individuals accumulate aberrant forms of both of these proteins. Tau becomes hyperphosphorylated and APP is cleaved by secretase to produce amyloid-beta (Aβ) protein which aggregates in the brain in plaque form. In general, the number of synapses is reduced and neurites are damaged in brain regions in which plaque is accumulated. This indicates that the amyloid-beta damages synapses and neurites (Mark P. M, Nature, 430, 631-639, 2004).

Research on pathogenetic mechanism has been actively conducted for the treatment of Alzheimer's disease. In particular, research on an inhibitor of beta-secretase and/or gamma-secretase producing amyloid-beta protein, a protease degrading accumulated amyloid-beta protein, and an inhibitor of acetylcholine esterase degrading acetylcholine have been intensively performed. Furthermore, research on a treatment for Alzheimer's disease using an inflammation inhibitor has been conducted since Alzheimer's disease is an aging-related chronic inflammatory disease.

The amount of amyloid-beta in the brain is determined by the balance between reactions for production and removal of the amyloid-beta. Accordingly, if the amyloid-beta removal is reduced, the amount of amyloid-beta is increased. Deficiency of neprilysin (NEP), which is an enzyme with activity for degrading amyloid-beta, results in accelerating extracellular accumulation of amyloid (Kanae Iijima-Ando, etc., J. Biol. Chem., 283(27), 19066-19076, 2008).

Abnormal neurites projected from a cell body of a neuron is related to neural diseases. Examples of the neural diseases are Alzheimer's disease, Parkinson's disease, depression, epilepsy, multiple sclerosis, and mania. In particular, epilepsy occurs due to death of neuron and gliosis of human hippocampus. Neurites are cleaved by the death of neuron. Multiple sclerosis is a chronic autoimmune disease occurring in the brain due to abnormalities of Nogo A, a neurite outgrowth inhibiting protein. Depression is a brain disorder caused by abnormalities of M6a, a neurite outgrowth-related protein. Alleviation of symptoms of mania has been reported in mice by activating a signal transduction pathway stimulating neurite outgrowth.

Mesenchymal stem cells (MSCs) are multipotent stem cells differentiating into mesodermal lineage cells such as osteocytes, chondrocytes, adipocytes, and myocytes or ectodermal lineage cells such as neurons. It has recently been reported that MSCs have a potential to differentiate into neuroglia in the brain, and thus attempts to differentiate MSCs into neurons have been made (Korean Patent Publication No. 10-2004-0016785, Feb. 25, 2004).

Among the MSCs, a bone marrow-derived MSC can be obtained from a patient. If the MSC is autologously transplanted, there is no immune rejection response, and thus can be clinically applied to patients. However, since bone marrow-derived MSC collection requires various stages of complicated medical treatments, bone marrow donation is time-consuming, psychologically and physically painful and expensive. However, since an umbilical cord blood-derived MSC is simply obtained from an umbilical cord, and the umbilical cord blood preservation industry is being actively developed, and donors are easily found due to the umbilical cord blood infrastructure, MSCs are easily obtained. Furthermore, MSCs obtained from allogeneic cord blood do not exhibit an immune response after transplantation, thereby exhibiting immunological stability.

All the cited references are incorporated herein by reference in their entireties.

DETAILED DESCRIPTION OF THE INVENTION

Technical Problem

For the treatment of neural diseases using stem cells, differentiation of stem cells into neurons needs to be performed in advance, or stem cells need to be administered with materials differentiating the stem cells into neurons according to the conventional methods.

One or more embodiments of the present invention include a cellular treatment method for a neural disease without differentiating stem cells into neurons.

One or more embodiments of the present invention include a composition for preventing and treating a neural disease comprising MSCs.

One or more embodiments of the present invention include a method of preventing of neurocytoxicity caused by amyloid-beta, preventing phosphorylation of tau protein in neurons, preventing neurite damage, and inducing expression of neprilysin in neurons or microglial cells.

One or more embodiments of the present invention include a kit for preventing neurocytoxicity caused by amyloid-beta, preventing phosphorylation of tau protein in neurons, preventing neurite damage, and inducing expression of neprilysin in neurons or microglial cells Technical Solution Inventors of the present invention have found that neurocytoxicity caused by amyloid-beta, phosphorylation of tau protein in neurons, and damage of neurites are prevented, and expression of neprilysin is induced in neurons or microglial cells when neurons or microglial cells treated with or without amyloid-beta are co-cultured with MSCs, a culture solution of MSCs, or proteins contained in the culture solution of MSCs.

Advantageous Effects

Neurocytoxicity caused by amyloid-beta is prevented, phosphorylation of tau protein in neurons is prevented, expression of neprilysin is induced in neurons or microglial cells, and damage of neurites is prevented when neurons or microglial cells are co-cultured with MSCs, a culture solution of MSCs, proteins contained in the culture solution of MSCs, and/or a signal transduction system-stimulating factor inducing expression of the proteins.

A composition including MSCs, a culture solution of MSCs, proteins contained in the culture solution of MSCs, or a signal transduction system-stimulating factor inducing expression of the proteins according to the present invention may be used as an effective cellular treatment composition for the prevention and treatment of neural diseases.

In addition, there are provided a method of and a kit for preventing neurocytoxicity caused by amyloid-beta, preventing phosphorylation of tau protein in neurons, preventing damage of neurites, and inducing expression of Neprilysin in neurons using MSCs, a culture solution of MSCs, proteins contained in the culture solution of MSCs, and/or a signal transduction system-stimulating factor inducing expression of the proteins.

BRIEF DESCRIPTION OF THE DRAWINGS

The patent or application file contains at least one drawing/photograph executed in color. Copies of this patent or patent application publication with color drawing(s)/picture(s) will be provided by the Office upon request and payment of the necessary fee.

The above and other features and advantages of the present invention will become more apparent by describing in detail exemplary embodiments thereof with reference to the attached drawings in which.

BEST MODE FOR CARRYING OUT THE INVENTION

According to embodiments of the present invention, damage of neurons caused by amyloid-beta may be prevented or repaired when the neurons are co-cultured with mesenchymal stem cells (MSCs), which are not differentiated into neurons, without direct contact between the neurons and the MSCs. In addition, the inventors of the present invention have found that damage of neurons by amyloid-beta may be prevented or repaired when co-cultured with a culture solution of MSCs or a specific protein contained in the culture solution.

Figure 3:
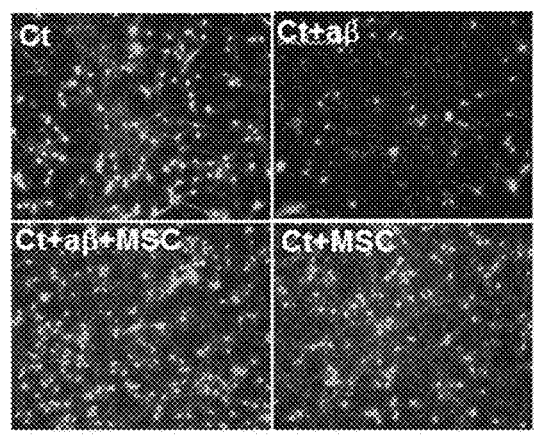
FIG. 3 illustrates results of fluorescent staining to explain effects of co-culturing neurons with human UCB-derived MSCs on death of neuron caused by amyloid-beta (Aβ42)

When neurons treated with 10 μM of amyloid-beta42 (Aβ42) for 24 hours (Ct+Aβ shown in FIGS. 1 and 3) are compared with untreated neurons (Ct shown in FIG. 3), most neurons treated with Aβ42 die. However, if the damaged neural cells are co-cultured with umbilical cord blood (UCB)-derived MSCs, death of neuron is prevented and cell maturation is increased (Ct+Aβ+MSC of FIG. 3 and FIG. 4). The effects of the UCB-derived MSCs on the prevention of death of neuron caused by amyloid-beta may also be observed in bone marrow-derived MSCs (Cortex/Aβ/BM-MSC of FIG. 5). When cerebral cortex-derived neurons and MSCs are co-cultured in the same culture medium in the presence of Aβ42 for 24 hours, the same result as shown in Ct+Aβ+MSC of FIG. 3 is obtained. This indicates that damaged neurons by Aβ42 may be repaired and the damage of neurons by Aβ42 may be prevented if the neurons are co-cultured with MSCs.

Figure 6:
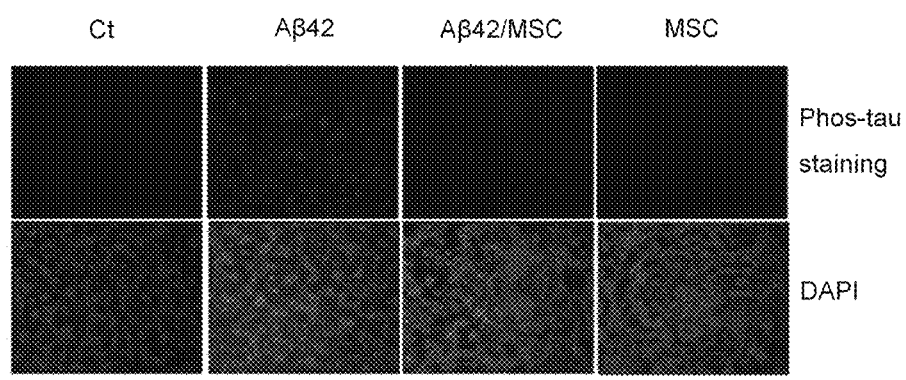
FIG. 6 illustrates neurons fluorescent stained using an anti-phosphor-tau antibody.

In addition, phosphorylation of tau protein, which is rapidly phosphorylated by Aβ42, is prevented by co-culturing the tau protein with human UCB-derived MSCs (FIG. 6).

Figure 7:
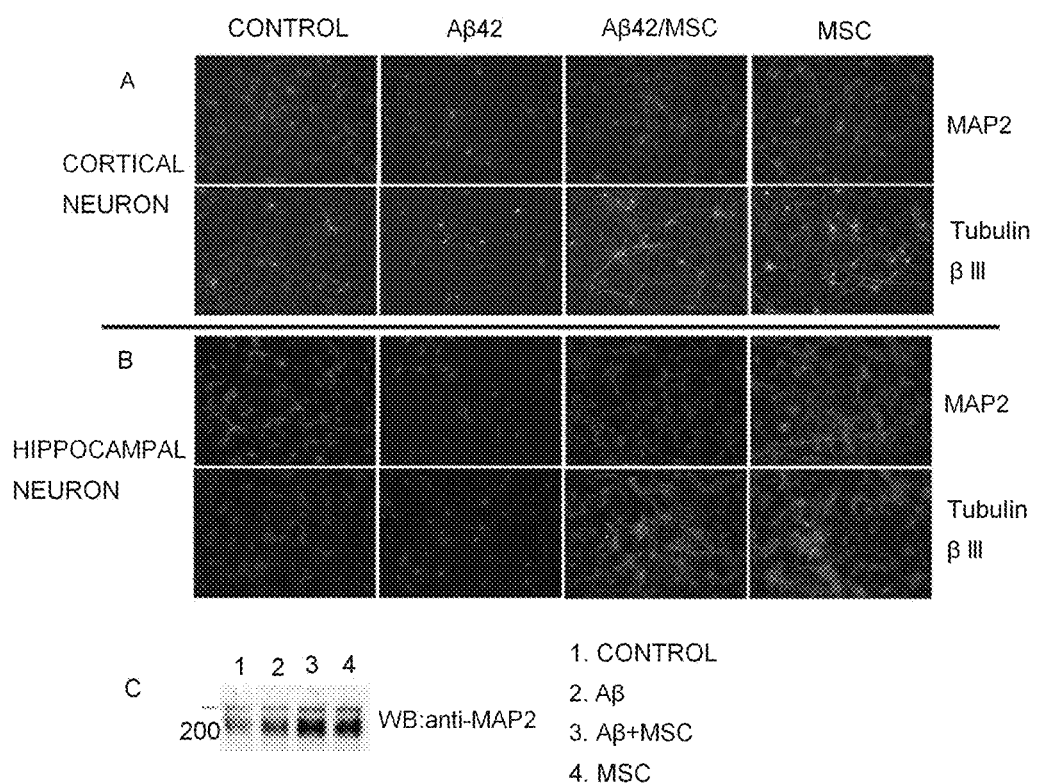
FIG. 7 illustrates neurons treated with Aβ42, co-cultured with MSCs, and stained using immunofluorescent staining.

As a result of observing neurons using antibodies against Tubulin β III and MAP2, i.e., markers of neurons, neurites are damaged and cleaved and the shape of the neurons is condensed in neurons treated with Aβ42 due to toxicity. However, when the neurons are co-cultured with the UCB-derived MSCs, the neurites are maintained in the neurons and differentiation and maturation of the neurons are accelerated (FIG. 7).

As a result of observing expression of neprilysin (NEP), known as protein degrading and removing Aβ42, the expression of NEP is reduced in neurons treated with Aβ42. However, when the neurons are co-cultured with UCB-derived MSCs, the expression of NEP is increased in the protein level and mRNA level (FIG. 8A). FIG. 8B illustrates stained neurons using an anti-NEP antibody. If the neurons are treated with Aβ42, the portion stained in red is considerably reduced, thereby indicating that the expression of NEP is reduced in the neurons. However, if the neurons are co-cultured with MSCs, the expression of the NEP is increased. These results are also observed in experiments using bone marrow-derived MSCs as well as UCB-derived MSCs (FIG. 8C). Thus, when a neural cell treated with or without Aβ42 is co-cultured with MSCs, the expression level of NEP in the neural cell is increased in mRNA and protein level. The MSCs includes UCB-MSCs and BM-MSCs.

Figure 9:
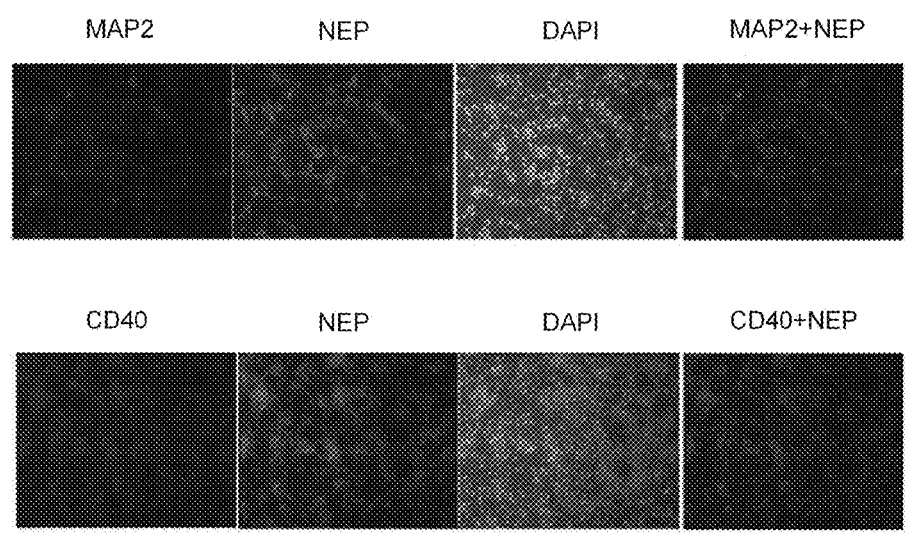
FIG. 9 illustrates expression of neprilysin in neurons and microglial cells when neurons and microglial cells treated with Aβ42 are co-cultured with MSCs.

Furthermore, it is also identified that UCB-derived MSCs induce the expression of NEP not only in the neurons (neurons) but also in microglial cells, which are known as macrophage of the brain and remove toxic substances accumulated in the brain, for example, Aβ of Alzheimer's disease (FIG. 9).

Figure 10:
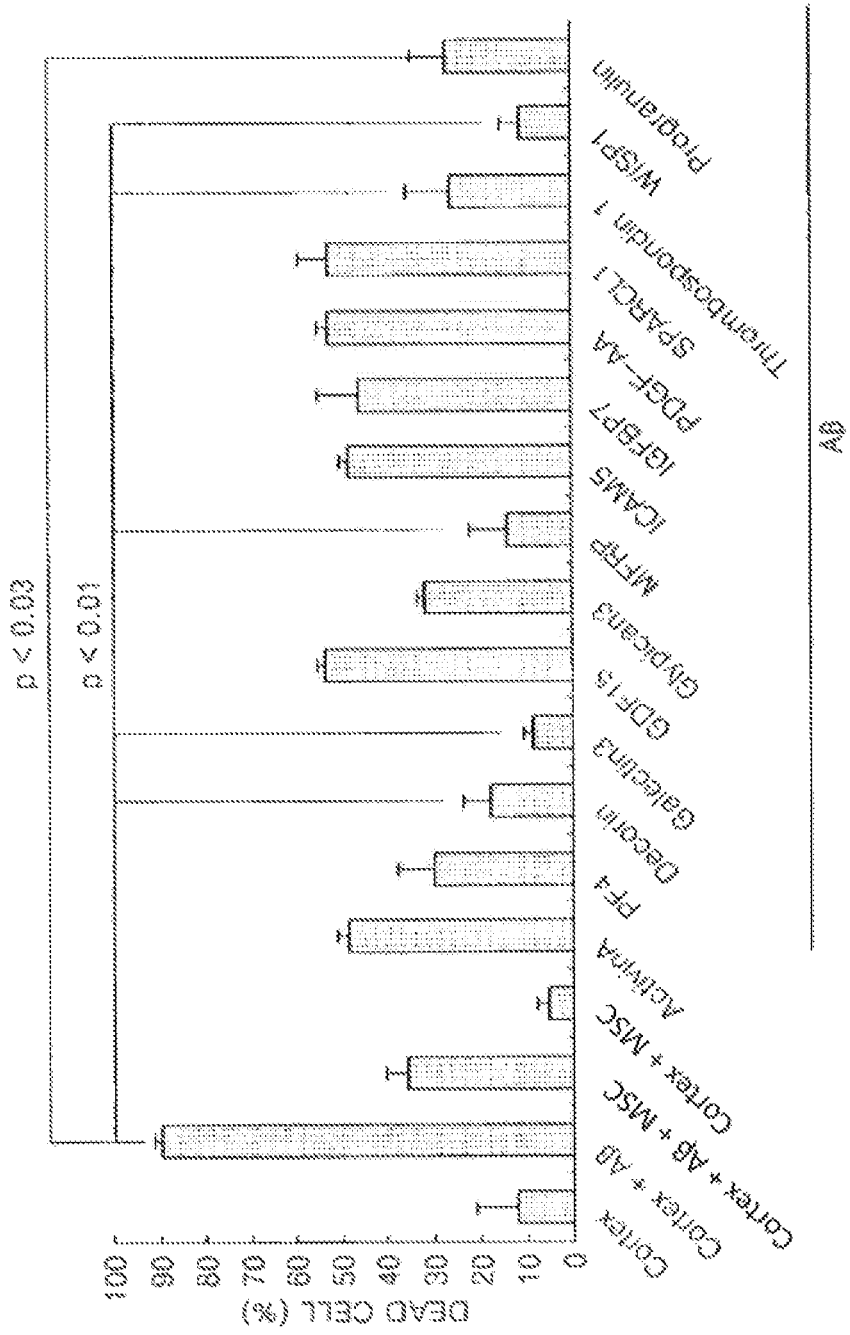
FIG. 10 is a graph illustrating the percentage of dead neurons treated with Aβ42 and co-cultured with proteins secreted from MSCs.
Figure 11:
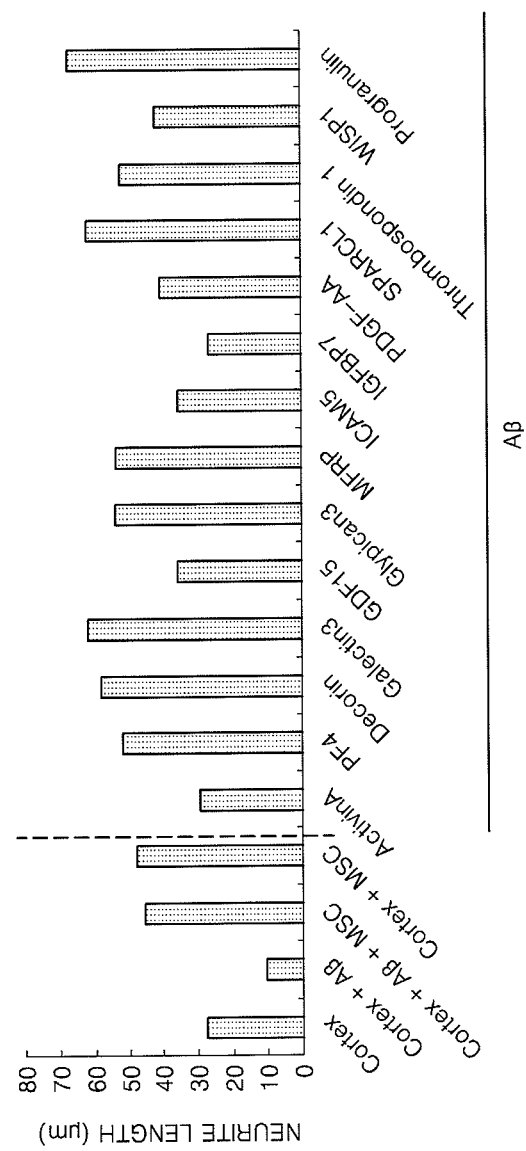
FIG. 11 is a graph illustrating the length of neurites of neurons cultured with Aβ42 and proteins secreted from MSCs.

Since the effects described above are obtained by co-culturing the MSCs and the neurons without direct contact therebetween, it is considered that substances secreted from the MSCs cause the effects. Proteins that are not expressed or rarely expressed when MSCs are singly cultured, but increasingly expressed in the MSCs when the neurons and the MSCs are co-cultured are analyzed. As a result, it is identified total 14 proteins are related to the prevention of toxicity caused by Aβ42 and differentiation and maturation of the neurons. The 14 proteins are activin A, platelet factor 4 (PF4), decorin, galectin 3, growth differentiation factor 15 (GDF15), glypican 3, membrane-type frizzled-related protein (MFRP), intercellular adhesion molecule 5 (ICAM5), insulin-like growth factor binding protein 7 (IGFBP7), platelet-derived growth factor-AA (PDGF-AA), secreted protein acidic and rich in cysteine (SPARCL1), thrombospondin-1, wnt-1 induced secreted protein 1 (WISP1), and progranulin. When the neurons treated with Aβ42 and each of the proteins instead of the MSCs, the death of neuron is considerably reduced, and the length of neurites is significantly increased when compared to the neurons treated only with Aβ42 (FIGS. 10 and 11). In this regard, the 14 proteins described above will be described in more detail.

Activin A that is known as inhibin βA (INHBA) is a homodimer protein. It is known that INHBA is coded by an INHBA gene in humans. INHBA may have an amino acid sequence of NCBI Accession No.: NP_002183 (SEQ ID NO: 1).

Platelet factor 4 (PF4) that is known as chemokine (C-X-C motif) ligand 4 (CXCL4) is a small cytokine belonging to a CXC chemokine family. The gene for human PF4 is located on human chromosome 4. PF4 may have an amino acid sequence of NCBI Accession No.: NP_002610 (SEQ ID NO: 2).

Decorin is a proteoglycan having an average molecular weight of about 90 to about 140 kDa. Decorin belongs to a small leucine-rich proteoglycan (SLRP) family and includes a protein core having leucine repeats with glycosaminoglycan (GAG) consisting of chondroitin sulfate (CS) or dermatan sulfate (DS). Decorin may have an amino acid sequence of NCBI Accession No.: NP_001911 (SEQ ID NO: 3).

Galectin 3 that is known as LGAL3 (lectin, galactoside-binding, soluble 3) is a lectin binding to beta-galactoside. For example, galectin 3 may have an amino acid sequence of NCBI Accession No.: NP_919308 (SEQ ID NO: 4).

Growth differentiation factor 15 (GDF15) that is known as macrophage inhibitory cytokine 1 (MIC1) is a protein belonging to a transforming growth factor beta superfamily and controlling an inflammatory pathway in wounds and a cell death pathway in a diseases process. For example, GDF15 may have an amino acid sequence of NCBI Accession No.: NP_004855 (SEQ ID NO: 5).

Glypican 3 that is known as GPC3 is a protein belongs to a glypican family. For example, glypican 3 may have an amino acid sequence of NCBI Accession No.: NP_004475 (SEQ ID NO: 6). Glypican belongs to a heparan sulfate proteoglycan family and is attached to the surface of cells through a covalent bond with glycosylphosphatidylinositol (GPI).

Membrane frizzled-related protein (MFRP), for example, may have an amino acid sequence of NCBI Accession No.: NP_113621 (SEQ ID NO: 7).

Intercellular adhesion molecule 5 (ICAM5) that is known as telencephalin belongs to an ICAM family. ICAM is a type I transmembrane glycoprotein, contains 2 to 9 immunoglobulin pseudo C2 type domains, and binds to leukocyte adhesion lymphocyte function-associated antigen 1 (LFA-1) protein. For example, ICAM5 may have an amino acid sequence of NCBI Accession No.: NP_003250 (SEQ ID NO: 8).

Insulin-like growth factor binding protein 7 (IGFBP7) belongs to an IGFBP family specifically binding to insulin-like growth factor (IGF). IGFBP7 is also known as IGF-binding protein-related protein 1 (IGFBP-rp1). For example, IGFBP7 may have an amino acid sequence of NCBI Accession No.: NP_001544 (SEQ ID NO: 9).

Platelet-derived growth factor AA (PDGF-AA) belongs to PDGF. PDGF-AA is a homodimer glycoprotein including PDGF alpha polypeptide that is known as two PDGFA. PDGF is a protein controlling the growth and differentiation of cells. PDGF is also related to angiogenesis. For example, PDGFA may have an amino acid sequence of NCBI Accession No.: XP_001126441 (SEQ ID NO: 10).

For example, secreted protein acidic and rich in cysteines-like 1 (SPARCL1) may have an amino acid sequence of NCBI accession No.: NP_004675 (SEQ ID NO: 11).

Thrombospondin 1 (TSP1) is a homotrimeric protein bound through a disulfide. Thrombospondin 1 is an adhesive glycoprotein that mediates cell-to-cell and cell-to-matrix interactions. Thrombospondin 1 can bind to fibrinogen, fibronectin, laminin, and type V collagen. For example, Thrombospondin 1 may have an amino acid sequence of NCBI Accession No.: NP_003237 (SEQ ID NO: 12).

WNT1 inducible signalling pathway protein 1 (WISP1) that is known as CCN4 belongs to a WISP protein subfamily and a connective tissue growth factor (CTGF) family. WNT1 is a cysteine-rich, glycosylated signalling proteins that mediate a variety of developmental process. A CTGF family members are characterized by four conserved cysteine-rich domains: an IGF binding domain, a vWF type C module, a thrombospondin domain and a C-terminal cystine knot-like domain. For example, WISP1 may have an amino acid sequence of NCBI Accession No.: NP_003873 (SEQ ID NO: 13).

Progranulin (PGN) is a precursor of granulin. Progranulin is a single precursor protein having 7.5 repeats of highly preserved 12-cysteine granulin/epithelin motif, and granulin (GRN) is cleaved from the progranulin and belongs to a secreted and glycosylated peptide family. Progranulin is also known as a proepithelin and a PC cell-derived growth factor. For example, progranulin may have an amino acid sequence of NCBI Accession No.: NP_001012497 (SEQ ID NO: 14).

If microglial cells and neurons are cultured in the presence of Interleukin-4 (IL-4), it was identified that the expression of neprilysin (NEP) is increased in the microglial cells and neurons. In addition, it was identified that amyloid plaque was reduced if UCB-derived MSCs (UCB-MSC) or IL-4 are administered to a mouse having Alzheimer's disease. It was also identified that the expression of NEP is increased in brain tissues including hippocampus and/or cerebral cortex if UCB-MSC or IL-4 are administered to a mouse having Alzheimer's disease. It was also identified that the expression of NEP is increased in microglial cell in brain tissues if UCB-MSC or IL-4 are administered to a mouse having Alzheimer's disease.

Interleukin-4 (IL-4) is a cytokine inducing differentiation of a naïve helper T cell (Th0 cell) into a Th2 cell. Th2 cell activated by IL-4 further produces IL-4. IL-4 may have an amino acid sequence of NCBI Accession Nos.: NP_000580 (SEQ ID NO: 30) or NP_067258.

The 14 proteins may include not only human-derived proteins but also mammal-derived proteins. For example, the mammal includes a rodent and the rodent may include for example, a mouse or a rat.

Even though the possibility of treating of neurodegenerative disorders, such as Alzheimer's disease, has been raised with recent research on tissue regenerative medicines using stem cells, currently available stem cell technology is not sufficiently developed to be applied to a wide range of memory loss in the brain such as Alzheimer's disease. However, the inventors of the present invention have found that MSCs reduce neurocytotoxicity caused by amyloid-beta, and accelerate differentiation and proliferation of neural stem cells in the brain. Thus, the possibility of developing a cellular preparation for the treatment of Alzheimer's disease and other neural diseases is raised. In addition, it has been found that several proteins secreted from MSCs have therapeutic effects on neural diseases such as Alzheimer's disease, and thus the potential for the prevention and treatment of neural diseases is increased.

The present invention provides a pharmaceutical composition for the prevention or treatment of a neural disease, including mesenchymal stem cells (MSCs), a culture solution of the MSCs, proteins contained in the culture solution of MSCs and/or a signal transduction system-stimulating factor inducing expression of the proteins. The neural disease may be a disease caused by a damaged neurite. The neural disease may be Alzheimer's disease, Parkinson's disease, depression, epilepsy, multiple sclerosis, mania, or any combination thereof.

A pre-dementia syndrome exhibiting mild cognitive impairment may be diagnosed using a neuropyschological test. It has been reported that about 12% of patients with mild cognitive impairment progress to Alzheimer's disease per year. Surprisingly, about 80% of patients with mild cognitive impairment progress to Alzheimer's disease after 6 years without any treatment. Thus, when a pharmaceutical composition according to the present invention is administered to patients with mild cognitive impairment, the progress to Alzheimer's disease may be prevented or delayed.

The present invention also provides a method and a kit for preventing neurocytotoxicity caused by treatment with amyloid-beta in neurons, preventing phosphorylation of tau protein in neurons, preventing neurite damage, and inducing expression of neprilysin in neurons using MSCs, a culture solution of MSCs, proteins contained in the culture solution of MSCs, or a signal transduction system-stimulating factor inducing expression of the proteins in vitro or in vivo. The kit may further include ingredients required for culturing the neurons.

The pharmaceutical composition including MSCs, a culture solution of MSCs, proteins contained in the culture solution of MSCs, or a signal transduction system-stimulating factor inducing expression of the proteins according to the present invention may be administered with other effective ingredients having effects on the prevention or treatment of Alzheimer's disease, Parkinson's disease, depression, epilepsy, multiple sclerosis, mania, etc.

The pharmaceutical composition may further include pharmaceutically acceptable additives in addition to effective ingredients, and may be formulated in a unit dosage formulation suitable for administering to a patient using any known method in the pharmaceutical field. For this purpose, a formulation for parenteral administration such as injection formulation or topical administration formulation may be used. For example, a formulation for parenteral administration such as injection formulation of a sterile solution or suspension, if required, using water or other pharmaceutically acceptable solvents, may be used. For example, a unit dosage formulation may be prepared using a pharmaceutically acceptable carrier or medium, e.g., sterile water, saline, vegetable oil, an emulsifier, a suspension, a surfactant, a stabilizer, an excipient, a vehicle, a preservative, and a binder.

The pharmaceutical formulation may be administered parenterally using any known method in the art. The parenteral administration may include a topical administration and a systematic administration. The topical administration may be performed by directly administering the pharmaceutical formulation into an injury region or peripheral regions of the injury region, for example, brain or spinal cord, peripheral regions thereof, or opposite regions thereof. The systematic administration may be performed by administering the pharmaceutical formulation into spinal fluid, vein or artery. The spinal fluid includes cerebrospinal fluid. The artery may be a region supplying blood to the injury region. In addition, the administration may be performed according to a method disclosed in (Douglas Kondziolka, Pittsburgh, Neurology, vol. 55, pp. 565-569, 2000). Specifically, a skull of a subject is incised to make a hole having a diameter of 1 cm and a suspension of MSCs in Hank's balanced salt solution (HBSS) is injected into the hole by employing a long-needle syringe and a stereotactic frame used to inject the suspension into a right position.

A dose of the MSCs may range from $1 \times 10^4$ to $1 \times 10^7$ cells/kg (body weight) per day, for example, from $5 \times 10^5$ to $5 \times 10^6$ cells/kg (body weight) per day, which can be administered in a single dose or in divided doses. However, it should be understood that the amount of the MSCs, for example, UCB-derived MSCs, actually administered to a patient should be determined in light of various relevant factors including type of diseases, severity of diseases, chosen route of administration, and body weight, age, and gender of an individual patient.

The present invention also provides a method of preventing or treating a neural disease of an individual, the method including administering a pharmaceutical composition comprising at least one selected from the group consisting of mesenchymal stem cells (MSCs) and a culture solution of the MSCs to the individual.

The administration used in the method may be a topical administration or a systematic administration. The pharmaceutical composition may be administered by an amount effective for preventing or treating the disease. It would be obvious to one of ordinary skill in the art that the effective amount may vary according to the conditions of the disease.

The pharmaceutical composition used in the method is the same as that described above. In the method, the MSCs contained in the pharmaceutical composition may be collected from not only autologous cells but also allogeneic cells from others and animals for medical experiments. Cells preserved in a frozen form may also be used. This therapeutic method is not limited to humans. In general, MSCs may also be applied to mammals as well as humans.

In the method, the neural disease may be a disease caused by at least one selected from the group consisting of amyloid-beta, hyperphosphorylation of tau protein, hypoexpression of neprilysin, and damage to neurites. The neural disease may be Alzheimer's disease, Parkinson's disease, depression, epilepsy, multiple sclerosis, or mania.

The amyloid-beta (Aβ) used herein indicates a major element of amyloid plaque found in the brain of a patient having Alzheimer's disease. The amyloid-beta (Aβ) may be a peptide including an amino acid derived from the C-terminal of amyloid precursor protein (APP) that is a transmembrane glycoprotein. The Aβ may be produced from APP by a continuous operation of β-secretase and γ-secretase. For example, the Aβ may include 39 to 43 amino acids, for example 40 to 42 amino acids. The Aβ may include 672-713 residues (Aβ42) or 672-711 residues (Aβ40) of an amino acid sequence of NCBI Accession No.: NP_000475 (SEQ ID NO: 19) which is human amyloid-beta A4 protein isoform precursor (APP). The amyloid-beta (Aβ) may be derived from a mammal. For example, the Aβ may be derived from a human or a mouse.

The "tau protein" used in this specification is a microtubule-associated protein found in neurons of a central nervous system. The tau protein interacts with tubulin to stabilize microtubule and promotes tubulin assembly of the microtubule. It is known that a cerebral tissue includes 6 different tau isoforms. It is known that hyperphosphorylation of tau protein is related to the outbreak of Alzheimer's disease. Tau protein is microtubule-associated protein having high solubility. In humans, tau protein is mainly found in neurons rather than non-neuron cells. One of the functions of tau protein is to control stabilization of axonal microtubule. For example, tau protein may be microtubule-associated protein tau isoform 2 having an amino acid sequence of NCBI Accession No.: NP_005901 (SEQ ID NO: 20). The tau protein may be derived from a mammal. For example, the tau protein may be derived from a human or a mouse.

Neprilysin is a zinc-dependent metalloprotease enzyme decomposing a large number of small secreted peptides. Neprilysin decomposes amyloid-beta that causes Alzheimer's disease if amyloid-beta is abnormally misfolded and aggregated in neural tissues. For example, neprilysin may have an amino acid sequence of NCBI Accession No.: NP_000893 (SEQ ID NO: 21). The neprilysin may be derived from a mammal. For example, the neprilysin may be derived from a human or a mouse.

The present invention also provides a method of reducing amyloid plaque in neural tissues, the method including culturing the neural tissues in the presence of at least one selected from the group consisting of mesenchymal stem cells (MSCs) and a culture solution of the MSCs.

In the method, the neural tissues such as neurons may be cultured in vitro or in vivo. The in vitro culture may be performed in a culture medium for MSCs and/or neural tissues such neurons which is known in the art. The MSCs and neural tissues such as neurons may be cultured with or without direct contact therebetween. For example, the MSCs and neural tissues such as neurons may be cultured by being separated from each other by a membrane with pores. The membrane may have a pore size and configuration sufficiently large for biologically active materials in the culture medium for the MSCs to pass through the pore but for cells not to pass therethrough. The biologically active materials may be proteins, sugars and nucleic acids. The membrane may be disposed such that the MSCs are cultured on the membrane and the neural tissues such as neurons are cultured below the membrane so that the biologically active materials pass through the membrane to the below of the membrane by the gravity.

The in vivo culture may further include administering at least one selected from the group consisting of MSCs and a culture solution of the MSCs into an individual. The administration may be a topical administration or a systematic administration. An effective amount for reducing the amount of plaque may be administered. It would be obvious to one of ordinary skill in the art that the effective amount may vary according to the conditions of the disease. The individual may be any animal in need of reducing amyloid plaque in it's neural tissues. The animal may include a mammal. The mammal may include a human, a mouse or a rat.

The reducing of amyloid plaque in the neural tissues may be reducing the amount of amyloid plaque in the neural tissues compared to that of amyloid plaque when the neural tissues such as neurons are cultured in the absence of the MSCs and a culture solution of the MSCs.

The term "amyloid plaque" used in this specification may be an insoluble fibrous protein aggregates including amyloid beta. The amyloid plaque may be present within a cell, on the cell membrane and/or in a space between cells.

The term "neural tissues" used herein, include central nerve system, for example, brain tissues. The brain tissues include cerebral tissues and hippocampus. The cerebral tissues include cerebral cortex. The neural tissues include neural cells as well as the neural tissues per se. The neural cells include neuronal cells and/or microglial cells. The culturing of the neural tissues includes culturing the neural cells such as neuronal cell and/or microglial cells in vivo or in vitro.

The present invention also provides a method of reducing the degree of phosphorylation of tau protein in neurons, the method including culturing the neurons in the presence of at least one selected from the group consisting of mesenchymal stem cells (MSCs) and a culture solution of the MSCs.

The culturing is described above with reference to the method of reducing amyloid plaque.

The reducing of phosphorylation of tau protein in the neurons may be reducing the amount of phosphorylation of tau protein compared to that of phosphorylation of tau protein when the neurons are cultured in the absence of the MSCs and a culture solution of the MSCs.

The present invention also provides a method of increasing expression of neprilysin in neurons or microglial cells, the method including culturing the neurons or microglial cells in the presence of at least one selected from the group consisting of mesenchymal stem cells (MSCs) and a culture solution of the MSCs.

The culturing is described above with reference to the method of reducing amyloid plaque in the neural tissues. The increasing of neprilysin expression in the neurons or microglial cells may be increasing neprilysin expression in the neurons or microglial cells compared to neprilysin expression in the neurons or microglial cells when the neurons or microglial cells are cultured in the absence of the MSCs and a culture solution of the MSCs.

The present invention also provides a method of increasing growth of neurites of neurons, the method including culturing the neurons in the presence of at least one selected from the group consisting of mesenchymal stem cells (MSCs) and a culture solution of the MSCs.

The culturing is described above with reference to the method of reducing amyloid plaque in the neural tissues. The neurons may be normal neurons or neurons having damaged neurites, for example, by Aβ. The increasing of neurites growth of the neurons may be increasing of neurites growth of the neurons compared to neurites growth of the neurons when the neurons are cultured in the absence of the MSCs and a culture solution of the MSCs.

The present invention also provides a method of preventing or treating a neural disease of an individual, the method including administering a pharmaceutical composition including at least one selected from the group consisting of activin A, PF4, decorin, galectin 3, GDF15, glypican 3, MFRP, ICAM5, IGFBP7, PDGF-AA, SPARCL1, thrombospondin-1, WISP1, progranulin, IL-4, a factor inducing expression thereof, and any combination thereof.

The administration used in the method may be a topical administration or a systematic administration. An effective amount for preventing or treating the neural disease may be administered. It would be obvious to one of ordinary skill in the art that the effective amount may vary according to the conditions of the disease.

The pharmaceutical composition used in the method is the same as that described above.

In the method, the neural disease may be a disease caused by at least one selected from the group consisting of amyloid-beta, hyperphosphorylation of tau protein, hypoexpression of neprilysin, and damage to neurites. The neural disease may be Alzheimer's disease, Parkinson's disease, depression, epilepsy, multiple sclerosis, or mania.

The present invention also provides a method of reducing amyloid plaque in neural tissues, the method including culturing the neural tissues in the presence of at least one selected from the group consisting of activin A, PF4, decorin, galectin 3, GDF15, glypican 3, MFRP, ICAM5, IGFBP7, PDGF-AA, SPARCL1, thrombospondin-1, WISP1, progranulin, IL-4, a factor inducing expression thereof, and any combination thereof.

In the method, the neural tissues such as neurons may be cultured in vitro or in vivo. The in vivo culture may further include administering at least one selected from the group consisting of activin A, PF4, decorin, galectin 3, GDF15, glypican 3, MFRP, ICAM5, IGFBP7, PDGF-AA, SPARCL1, thrombospondin-1, WISP1, progranulin, IL-4, a factor inducing expression thereof, and any combination thereof to the individual. The administration may be a topical administration or a systematic administration. An effective amount for reducing the amount of the plaque may be administered. It would be obvious to one of ordinary skill in the art that the effective amount may vary according to the conditions of the disease. For example, each one selected from the group consisting of activin A, PF4, decorin, galectin 3, GDF15, glypican 3, MFRP, ICAM5, IGFBP7, PDGF-AA, SPARCL1, thrombospondin-1, WISP1, progranulin, IL-4, a factor inducing expression thereof, and any combination thereof may be administered in amount from about 1 ng/kg body weight to about 100 mg/kg body weight, for example, about 10 ng/kg body weight to about 50 mg/kg body weight. The administered formulation may further include additives such as water, a culture medium, a buffer, or an excipient. The individual may be any animal in need of reducing amyloid plaque in it's neural tissues. The animal may include a mammal. The mammal may include a human, a mouse or a rat.

The amyloid plaque may be reduced in the presence of at least one selected from the group consisting of activin A, PF4, decorin, galectin 3, GDF15, glypican 3, MFRP, ICAM5, IGFBP7, PDGF-AA, SPARCL1, thrombospondin-1, WISP1, progranulin, IL-4, a factor inducing expression thereof, and any combination thereof when compared to in the absence thereof.

The present invention also provides a method of reducing the degree of phosphorylation of tau protein in neurons, the method including culturing the neurons in the presence of at least one selected from the group consisting of activin A, PF4, decorin, galectin 3, GDF15, glypican 3, MFRP, ICAM5, IGFBP7, PDGF-AA, SPARCL1, thrombospondin-1, WISP1, progranulin, IL-4, a factor inducing expression thereof, and any combination thereof.

The culturing is described above with reference to the method of reducing amyloid plaque in the neural tissues. The degree of phosphorylation of tau protein in neurons may be reduced in the presence of at least one selected from the group consisting of activin A, PF4, decorin, galectin 3, GDF15, glypican 3, MFRP, ICAM5, IGFBP7, PDGF-AA, SPARCL1, thrombospondin-1, WISP1, progranulin, IL-4, a factor inducing expression thereof, and any combination thereof when compared to in the absence thereof.

The present invention also provides a method of increasing expression of neprilysin of neurons or microglial cells, the method including culturing the neurons or microglial cells in the presence of at least one selected from the group consisting of activin A, PF4, decorin, galectin 3, GDF15, glypican 3, MFRP, ICAM5, IGFBP7, PDGF-AA, SPARCL1, thrombospondin-1, WISP1, progranulin, IL-4, a factor inducing expression thereof, and any combination thereof.

The culturing is described above with reference to the method of reducing amyloid plaque in the neural tissues. The expression of neprilysin of neurons or microglial cells may be increased in the presence of at least one selected from the group consisting of activin A, PF4, decorin, galectin 3, GDF15, glypican 3, MFRP, ICAM5, IGFBP7, PDGF-AA, SPARCL1, thrombospondin-1, WISP1, progranulin, IL-4, a factor inducing expression thereof, and any combination thereof when compared to in the absence thereof.

The present invention also provides a method of increasing growth of neurites of neurons, the method including culturing the neurons in the presence of at least one selected from the group consisting of activin A, PF4, decorin, galectin 3, GDF15, glypican 3, MFRP, ICAM5, IGFBP7, PDGF-AA, SPARCL1, thrombospondin-1, WISP1, progranulin, IL-4, a factor inducing expression thereof, and any combination thereof.

The culturing is described above with reference to the method of reducing amyloid plaque in the neural tissues. The neurons may be normal neurons or neurons having damaged neurites, for example, by Aβ. The growth of neurites of neurons may be increased in the presence of at least one selected from the group consisting of activin A, PF4, decorin, galectin 3, GDF15, glypican 3, MFRP, ICAM5, IGFBP7, PDGF-AA, SPARCL1, thrombospondin-1, WISP1, progranulin, IL-4, a factor inducing expression thereof, and any combination thereof when compared to in the absence thereof.

The "mesenchymal stem cell (MSC)" used herein may be a MSC isolated from at least one selected from a group consisting of a mammalian, e.g. human, embryonic yolk sac, placenta, umbilical cord, umbilical cord blood, skin, peripheral blood, bone marrow, adipose tissue, muscle, liver, neural tissue, periosteum, fetal membrane, synovial membrane, synovial fluid, amniotic membrane, meniscus, anterior cruciate ligament, articular chondrocytes, decidous teeth, pericyte, trabecular bone, infra patellar fat pad, spleen, thymus, and other tissues including MSCs or expanded by culturing the isolated MSC.

As used herein, the "umbilical cord blood" refers to the blood taken from the umbilical cord vein which links the placenta of mammals including humans with a newborn baby thereof. The "umbilical cord blood-derived MSC" as used herein refers to a MSC which is isolated from the umbilical cord blood of mammals, for example, humans or a MSC expanded by culturing the isolated UCB-MSC.

The "treating" used herein refers to: preventing the manifestation of a not-yet-diagnosed disease or disorder in animals, for example, mammals including humans, which are prone to acquiring such diseases or disorders; inhibiting the development a disease; or relieving a disease.

Terminology that is not defined herein have meanings commonly used in the art.

Any known method, for example, a method disclosed in Korean Patent No. 489248 may be used to isolate mononuclear cells including MSCs from umbilical cord blood. For example, a Ficoll-Hypaque density gradient method may be used, but the method is not limited thereto. Specifically, umbilical cord blood collected from the umbilical vein after childbirth and before the placenta is removed is centrifuged using a Ficoll-Hypaque gradient to obtain mononuclear cells. The mononuclear cells were washed several times to remove impurities. The isolated mononuclear cells may be subjected to isolation and cultivation of MSCs or to be frozen for long-term safekeeping at a very low temperature until use.

Any known method may be used for MSC isolation from the umbilical cord blood and cultivation of the MSC (Korean patent Publication No. 2003-0069115, and Pittinger M F, *Science,* 284: 143-7, 1999; and Lazarus H M, etc. *Bone Marrow Transplant,* 16: 557-64, 1995).

First, collected umbilical cord blood is centrifuged using a Ficoll-Hypaque gradient to isolate mononuclear cells including hematopoietic stem cells and MSCs, and the mononuclear cells are washed several times to remove impurities. The mononuclear cells are cultured in a culture dish with an appropriate density. Then, the mononuclear cells are proliferated to form a monolayer. Among the mononuclear cells, MSCs proliferate in a homogenous and spindle-shaped long colony of cells when observed using a phase contrast microscope. The grown cells are repeatedly sub-cultured to obtain a desired number of cells.

Cells contained in the composition according to the present invention may be preserved in a frozen form using known methods. (Campos, etc., Cryobiology 32: 511-515, 1995). A culture medium used for the frozen form may include 10% dimethylsulfoxide (DMSO) and one of 10 to 20% fetal bovine serum (FBS), human peripheral blood, or plasma or serum of umbilical cord blood. The cells may be suspended such that about $1 \times 10^6$ to $5 \times 10^6$ cells exist in 1 mL of the medium.

The cell suspension is distributed into glass or plastic ampoules for deep freezing, and then the ampoules may be sealed and put in a deep freezer kept at a programmed temperature. In this regard, for example, a freeze-program that controls the freezing rate at −1° C./min is used so that cell damage during thawing is minimized. When the temperature of the ampoules reaches less than −90° C., it may be transferred into a liquid nitrogen tank and maintained at less than −150° C.

To thaw the cells, the ampoules have to be quickly transferred from the liquid nitrogen tank into a 37° C. water bath. The thawed cells in the ampoules are quickly placed in a culture vessel containing a culture medium under an aseptic condition.

In the present invention, the medium used in the isolation and cultivation of the MSCs may be any medium for general cell culture well-known in the art containing 10 to 30% FBS, human peripheral blood, or plasma or serum of umbilical cord blood. For example, the culture medium may be Dulbecco's modified eagle medium (DMEM), minimum essential medium (MEM), α-MEM, McCoys 5A medium, Eagle's basal medium, Connaught Medical Research Laboratory (CMRL) medium, Glasgow minimum essential medium, Ham's F-12 medium, Iscove's modified Dulbecco's medium (IMDM), Liebovitz' L-15 medium, or Roswell Park Memorial Institute (RPMI) 1640 medium, for example, DMEM. The cells may be suspended at the concentration of $5 \times 10^3$ to $2 \times 10^4$ cells per 1 ml of the medium.

Furthermore, the cell culture medium of the present invention may further include one or more auxiliary components. The auxiliary components may be fetal bovine serum, horse serum or human serum; and antibiotics such as Penicillin G, streptomycin sulfate, and gentamycin; antifungal agents such as amphotericin B and nystatin; and a mixture thereof to prevent microorganism contamination.

Umbilical cord blood-derived cells do not express histocompatibility antigen HLA-DR (class II) which is the major cause of rejection after tissue or organ transplantation (Le Blanc, K C, *Exp Hematol,* 31:890-896, 2003; and Tse W T et al., *Transplantation,* 75:389-397, 2003). Since these cells can minimize the immune response after transplantation, for example, rejection of transplanted tissue or organs, autologous as well as allogeneic umbilical cord blood can be used. Frozen cells may also be used.

The culture solution of MSCs may be a culture solution used for culturing mammalian cells, for example, human bone marrow-derived MSCs, UCB-derived MSCs, adipose tissue-derived stem cells, embryonic yolk sac-derived MSCs, placenta-derived MSCs, skin-derived MSCs, peripheral blood-derived MSCs, muscle-derived MSCs, liver-derived MSCs, neural tissue-derived MSCs, periosteum-derived MSCs, umbilical cord-derived MSCs, fetal membrane-derived MSCs, synovial membrane-derived MSCs, synovial fluid-derived MSCs, amniotic membrane-derived MSCs, meniscus-derived MSCs, anterior cruciate ligament-derived MSCs, articular chondrocytes-derived MSCs, decidous teeth-derived MSCs, pericyte-derived MSCs, trabecular bone-derived MSCs, infra patellar fat pad-derived MSCs, spleen-derived MSCs, thymus-derived MSCs, and MSCs isolated from other tissues including MSCs, and/or cultured MSCs.

The culture medium may be for example, a cell culture medium containing FBS, or plasma or serum of human peripheral blood or umbilical cord blood. The cell culture medium may include, for example, DMEM, MEM, α-MEM, McCoys 5A medium, Eagle's basal medium, CMRL medium, Glasgow minimum essential medium, Ham's F-12 medium, Iscove's modified Dulbecco's medium (IMDM), Liebovitz' L-15 medium, and RPMI 1640 medium, but is not limited thereto.

The culture solution of MSCs according to the present invention may include at least one selected from the group consisting of activin A, PF4, decorin, galectin3, GDF15, glypican3, MFRP, ICAM5, IGFBP, PDGF-AA, SPARCL1, thrombospondin1, WISP1, and progranulin, IL-4, or a factor inducing at least one of the proteins.

The pharmaceutical composition according to the present invention may include at least one protein selected from the group consisting of activin A, PF4, decorin, galectin3, GDF15, glypican3, MFRP, ICAM5, IGFBP, PDGF-AA, SPARCL1, thrombospondin1, WISP1, and progranulin, IL-4, or a factor inducing at least one of the proteins as an active ingredient.

The factor inducing at least one of the proteins may be a signal transduction system-stimulating factor and any known factor. The factor may be the following examples, but is not limited thereto. The factor inducing galectin 3 may include at least one selected from the group consisting of phorbol 12-myristate 13-acetate (PMA) and a modified lipoprotein. The PMA or the lipoprotein is known to induce galectin 3 via protein kinase C (PKC), mitogen-activated protein kinase 1,2 (MAPK-1,2) and p38 kinase. The factor inducing PDGF-AA may include at least one selected from the group consisting of avian erythroblastosis virus E26 (v ets) oncogene homolog 1 (Ets-1) and lysophosphatidylcholine. Lysophosphatidylcholine is known to induce PDGF-AA via MAPK-1,2.

All cited references may be incorporated herein by reference in their entireties.

The present invention will be described in further detail with reference to the following examples. These examples are for illustrative purposes only and are not intended to limit the scope of the present invention.

EXAMPLES

Example 1: Isolation and Cultivation of Neural Stem Cells

Neural stem cells used herein were isolated as follows. Neural stem cells were isolated from the cerebral cortex and hippocampus of an embryonic day 14 (E14) Sprague-Dawley rat (Orient Bion Inc., Korea). First, the abdomen of a pregnant rat was incised, and the embryo was isolated using a scissors and forceps. The embryo was washed with a Hank's balanced salt solution (HBSS) for dissection and placed in a dish containing ice-cold HBSS. The cerebral cortex and hippocampus were isolated from the E14 embryo using needles and forceps under a microscope. The isolated cerebral cortex was pipetted 10 to 20 times into single cells in a serum-free culture solution using pipettes. The single cells were treated with poly-L-ornithine (15 μg/ml, Sigma, St. Louis, Mo.) at 37° C. for 16 hours and smeared on a cover slip coated with fibronectin (1 μg/ml, Sigma) for at least 2 hours. The single cells were cultured in a serum-free Neurobasal™ culture medium (GIBCO) supplemented with 20 ng/ml of basic fibroblast growth factor (bFGF) and B-27 serum-free supplement for about 2 to 4 days until about 70% of the bottom surface of the culture dish was covered with the single cells (70 to 80% confluence). The bFGF was removed and differentiation of the neuron cells was induced for 4 to 6 days. During the differentiation, the cells were incubated in a 5% $CO_2$ incubator at 37° C., while the culture medium and the B27 supplement were changed every other day and the bFGF was added thereto everyday. The differentiated neurons were used in the following examples.

Example 2: Isolation and Amplification of UCB-Derived MSCs

An umbilical cord blood (UCB) sample was collected from the umbilical vein right after childbirth with the mother's approval. Specifically, the umbilical vein was pricked with a 16-gauge needle connected to an UCB collection bag containing 44 mL of a citrate phosphate dextrose anticoagulant-1 (CPDA-1) anticoagulant (Green Cross Corp., Korea) such that the UCB was collected in the collection bag by gravity. The UCB thus obtained was handled within 48 hours after collection, and the viability of the monocytes was more than 90%. The collected UCB was centrifuged using a Ficoll-Hypaque gradient (density: 1.077 g/mL, Sigma) to obtain mononuclear cells and the mononuclear cells were washed several times to remove impurities. The cells were suspended in a minimal essential medium (α-MEM, Gibco BRL) supplemented with 10% to 20% of FBS (HyClone). The cells were introduced into the minimal essential medium supplemented with 10% to 20% of FBS to an optimized concentration, and cultured in a 5% $CO_2$ incubator at 37° C., while changing the culture medium twice a week. When the cultured cells formed a monolayer, and MSCs amplified in a spindle shape were identified using a phase contrast microscope, sub-cultures of the cells were repeated so as to sufficiently amplify the MSCs. The UCB-derived MSCs were cultured in α-MEM supplemented with 10 to 20% of FBS.

Example 3: Toxicity of Amyloid-Beta Protein

In order to prepare ideal conditions for an outbreak of Alzheimer's disease, the neurons differentiated as described in Example 1 were cultured in a serum-free Neurobasal™ culture medium without bFGF and B27 and including 10 μM of amyloid-beta protein fragment 1-42 (Aβ42, sigma, A9810) that is known to cause Alzheimer's disease. After 3 to 4 days of differentiation of the neural stem cells, morphological characteristics of the neural stem cells were observed using a microscope. If the differentiation into neurons was identified, the cells were treated with Aβ for 24 hours.

Figure 1:
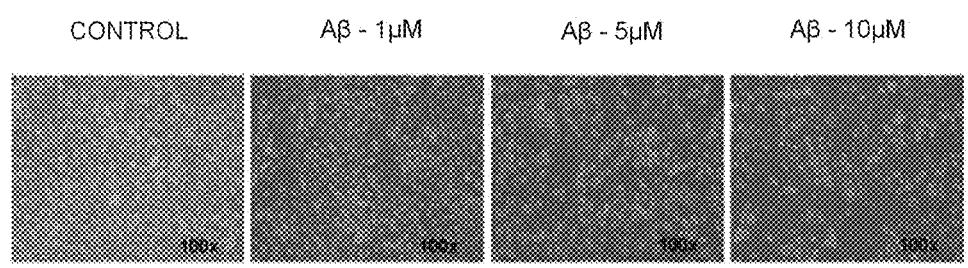
FIG. 1 illustrates optical microscopic images of live neurons untreated and treated with amyloid-beta for 24 hours.

FIG. 1 illustrates optical microscopic images of live neurons untreated and treated with amyloid-beta for 24 hours to measure morphological changes of the neurons. As the concentration of the amyloid-beta increased, the number of dead neurons increased. In FIG. 1, the control shows neurons cultured in a serum-free Neurobasal™ culture medium without amyloid-beta, the Aβ-1 μM, Aβ-5 μM, and Aβ-10 μM respectively show neurons cultured in culture media respectively including 1 μM, 5 μM, and 10 μM of amyloid-beta for 24 hours.

Example 4: Effects of Co-Culture of Human UCB-Derived MSCs and Neurons Treated with Amyloid-Beta on Death of Neuron When neurons treated with amyloid-beta were co-cultured with human UCB-derived MSCs, neurons damaged by toxic substances such as amyloid-beta were observed.

Figure 2:
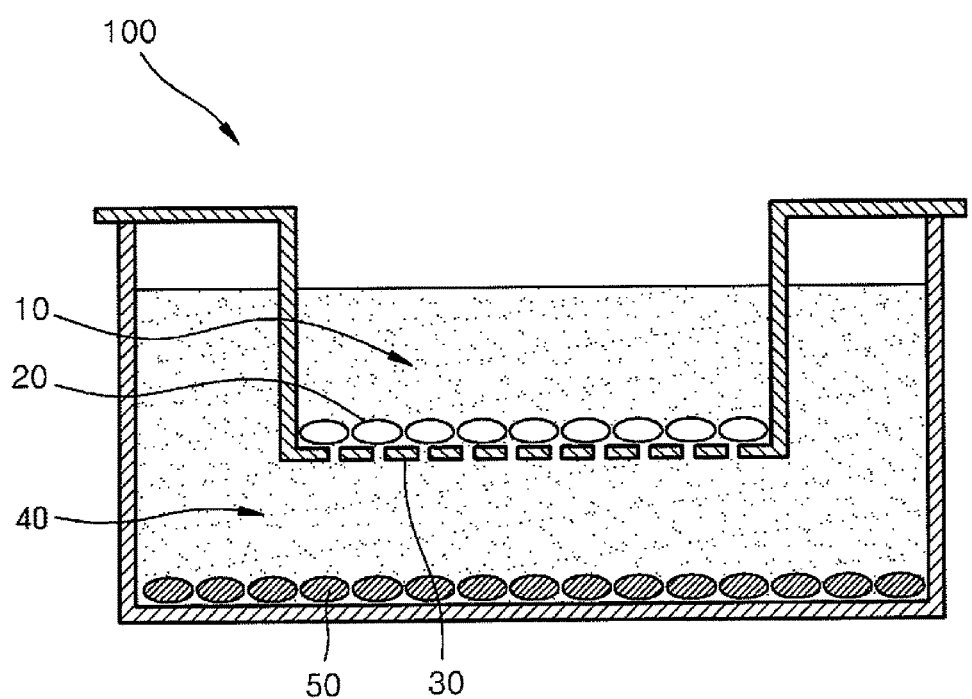
FIG. 2 shows a co-culture system for co-culturing neurons treated with amyloid-beta with human UCB-derived MSCs.

In particular, E14 embryo cerebral cortex stem cells and hippocampus stem cells were isolated, and the isolated stem cells were proliferated and differentiated into neurons in the same manner as described in Example 1, and then treated with 10 μM of amyloid-beta as in Example 3. After 12 hours of the amyloid-beta treatment, the neurons treated with the amyloid-beta were co-cultured with human UCB-derived MSCs in the presence of the amyloid-beta for 12 hours, so that the cells were cultured for 24 hours in total in the presence of the amyloid-beta. The co-culture was performed in a co-culture system as shown in FIG. 2. FIG. 2 shows a co-culture system for co-culturing neurons treated with amyloid-beta with human UCB-derived MSCs. Referring to FIG. 2, a co-culture system 100 includes an upper chamber 10 and a lower chamber 40, wherein the bottom of the upper chamber 10 includes a microporous membrane 30 having a pore size of about 1 μm. Human UCB-derived MSCs 20 were cultured in the upper chamber 10, and neurons 50 differentiated from cerebral cortex stem cells or hippocampus stem cells were cultured in the lower chamber 40. The upper chamber 10 and the lower chamber 40 may be separated from each other, and the lower surface of the bottom of the upper chamber 10 is spaced apart from the upper surface of the bottom of the lower chamber 40 by about 1 mm. The co-culture was performed by respectively culturing cells in the lower chamber 40 and the upper chamber 10, and adding the upper chamber 10 to the culture medium of the lower chamber 40.

Cerebral cortex and hippocampus-derived neurons untreated, cerebral cortex and hippocampus-derived neurons treated with amyloid-beta, and cerebral cortex and hippocampus-derived neurons untreated with amyloid-beta and co-cultured with MSCs were also cultured and observed. Damaged cerebral cortex and hippocampus-derived neurons and human UCB-derived MSCs were co-cultured for 24 hours after the amyloid-beta treatment, and then the degree of the damage of the neurons was observed using a microscope. The cultivation was performed using serum-free Neurobasal™ culture media (GIBCO) without bFGF and B27.

In order to quantitatively measure death of neuron caused by treatment with amyloid-beta, live and dead cells were measured using a fluorescent staining analysis. Cytoxicity was analyzed using a LIVE/DEAD™ viability/cytotoxicity assy kit for animal cells (Sigma, L3224). The kit includes calcein AM and ethidium homodimer, wherein the calcein AM is used to identify live cells, and the ethidium homodimer is used to identify dead cells. The calcein AM is a non-fluorescent cell permeable dye and converted into a green fluorescent calcein in a live cell by hydrolysis of acetoxymethyl ester by esterase in the cell. The ethidium homodimer cannot permeate a membrane of a live cell but permeates a damaged cell membrane and binds to nucleic acids of the cell to emit red fluorescence.

Cerebral cortex and hippocampus-derived neurons were cultured in a culture medium containing Aβ42 in a lower chamber 40 of the co-culture system 100 to directly treating the Aβ42 to the neurons. Dead cells were stained in red and live cells were stained in green by a live/dead staining. As a result, when cells treated with 10 μM Aβ42 for 24 hours (Ct+Aβ of FIG. 3) were compared with untreated cells (Ct of FIG. 3), green fluorescence was significantly reduced and a wide range of red fluorescence was observed by the treatment with Aβ42, thereby indicating that most neurons were dead by the treatment with Aβ42. However, if the damaged neural stem cells were co-cultured with UCB-derived MSCs in the co-culture system 100 shown in FIG. 2, death of the neurons was prevented and maturation of neuron was increased (Ct+Aβ+MSC of FIG. 3). This indicates that if neurons damaged by Aβ42 are co-cultured with UCB-MSCs, the damaged cells may be restored. In FIG. 3, Ct+Aβ+MSC shows cerebral cortex-derived neurons cultured in a serum-free Neurobasal™ culture medium including 10 μM of Aβ42 for 12 hours and then co-cultured with UCB-derived MSCs in the presence of 10 μM of Aβ42 for 12 hours. In addition, when cerebral cortex-derived neurons were cultured in a serum-free Neurobasal™ culture medium in the presence of 10 μM of Aβ42 in the lower chamber 40 and UCB-derived MSCs were simultaneously cultured in the same culture medium in the upper chamber 10 for 24 hours, the results were the same shown in the Ct+Aβ+MSC of FIG. 3. Thus, if neurons were co-cultured with UCB-MSCs, the neurons damaged by Aβ42 may be restored and the damage by Aβ42 may be prevented.

In FIG. 3, Ct shows cerebral cortex-derived neurons cultured in a serum-free Neurobasal™ culture medium without Aβ42 for 24 hours, Ct+Aβ shows cerebral cortex-derived neurons cultured in a serum-free Neurobasal™ culture medium including 10 μM of Aβ42 for 24 hours, Ct+Aβ+MSC shows cerebral cortex-derived neurons cultured in a serum-free Neurobasal™ culture medium including 10 μM of Aβ42 for 12 hours and then co-cultured with UCB-derived MSCs in the presence of 10 μM of Aβ42 for 12 hours, and Ct+MSC shows cerebral cortex-derived neurons cultured in a serum-free Neurobasal™ culture medium without Aβ42 for 12 hours and then co-cultured with UCB-derived MSCs for 12 hours.

Figure 4:
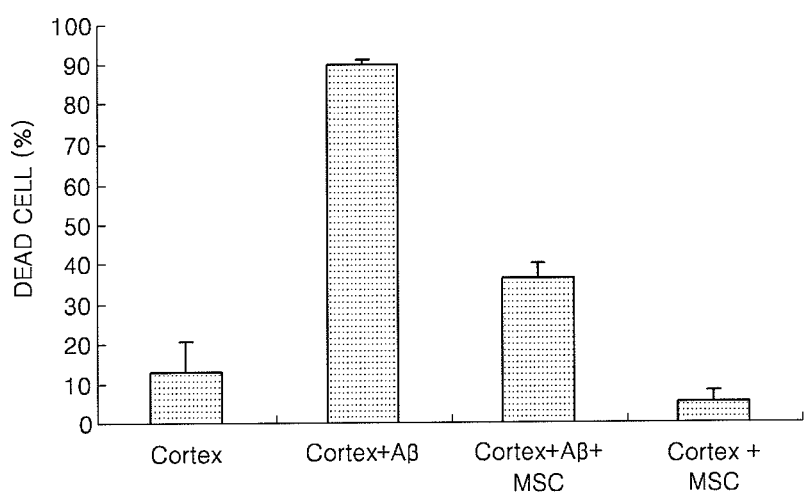
FIG. 4 is a graph illustrating the percentage of dead neurons to explain effects of co-culturing neurons with human UCB-derived MSCs on death of neuron caused by Aβ42.

FIG. 4 is a graph illustrating the percentage of dead neurons based on the results of FIG. 3. In FIG. 4, cortex shows the results of the control in which cerebral cortex-derived neurons were cultured in a culture medium without Aβ42, Cortex+Aβ shows the results of culturing cerebral cortex-derived neurons in a culture medium including 10 μM of Aβ42 for 24 hours, Cortex+Aβ+MSC shows the results of culturing cerebral cortex-derived neurons in a culture medium including 10 μM of Aβ42 for 12 hours and then co-culturing the cerebral cortex-derived neurons with human UCB-derived MSCs in the presence of 10 μM of Aβ42 for 12 hours, and Cortex+MSC shows the results of culturing cerebral cortex-derived neurons in a culture medium without Aβ42 for 12 hours and then co-culturing the cerebral cortex-derived neurons with human UCB-derived MSCs for 12 hours.

Example 5: Effects of Co-Culture of Human Bone Marrow-Derived MSCs and Neurons Treated with Amyloid-Beta on Death of Neuron Experiments were performed in the same manner as in Example 4 using bone marrow-derived MSCs (BM-MSC) collected from donated bone marrow. When neurons treated with Aβ were co-cultured with bone marrow-derived MSCs, death of neuron was prevented as in Examples 4 (Ct/Aβ/BM-MSC of FIG. 5).

Figure 5:
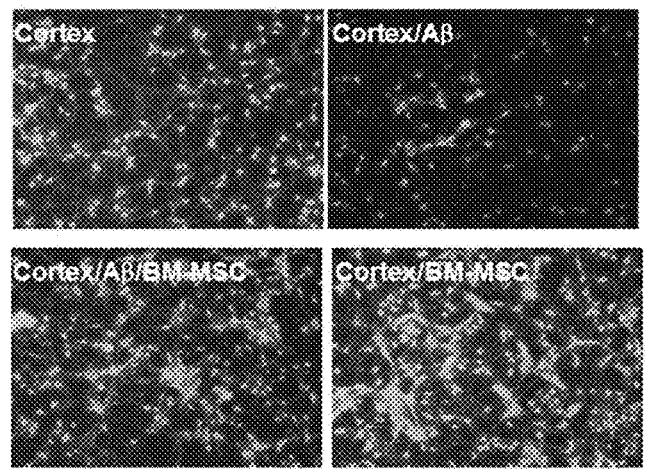
FIG. 5 illustrates results of fluorescent staining to explain effects of co-culturing neurons with human bone marrow-derived MSCs on death of neuron caused by Aβ42.

FIG. 5 illustrates results of fluorescent staining to explain effects of co-culturing neurons with human bone marrow-derived MSCs on death of neuron caused by Aβ42. In FIG. 5, Ct shows the results of the control in which cerebral cortex-derived neurons were cultured in a culture medium without Aβ, Ct+Aβ shows the results of culturing cerebral cortex-derived neurons in a culture medium including 10 μM of Aβ for 24 hours, Ct/Aβ/BM-MSC shows the results of culturing cerebral cortex-derived neurons in a culture medium including 10 μM of Aβ for 12 hours and then co-culturing the cerebral cortex-derived neurons with human bone marrow-derived MSCs in the presence of 10 μM of Aβ for 12 hours, and Ct+BM-MSC shows the results of culturing cerebral cortex-derived neurons in a culture medium without Aβ for 12 hours and then co-culturing the cerebral cortex-derived neurons with human bone marrow-derived MSCs for 12 hours.

Example 6: Effects of Co-Culture of Human UCB-Derived MSCs and Neurons Treated with Amyloid-Beta on Phosphorylation of Tau Protein FIG. 6 illustrates neurons stained using an anti-phosphor-tau antibody that is an antibody binding to phosphorylated tau by Aβ42, wherein tau is known as a protein inducing death of neuron. The anti-phosphor-tau antibody were conjugated with a red fluorescent Cy3 to visualize the binding of the anti-phosphor-tau antibody and the phosphor-tau.

The first row of FIG. 6 shows neurons stained with Cy3-conjugated anti-phosphor-tau antibody, and the second row of FIG. 6 shows neurons stained with 4',6-diamidino-2-phenylindole (DAPI). In the first row of FIG. 6, Ct shows the results of the control in which cerebral cortex-derived neurons were cultured in a culture medium without Aβ, Aβ42 shows the results of culturing cerebral cortex-derived neurons in a culture medium including 10 μM of Aβ for 24 hours, Aβ42/MSC shows the results of culturing cerebral cortex-derived neurons in a culture medium including 10 μM of Aβ for 12 hours and then co-culturing the cerebral cortex-derived neurons with human UCB-derived MSCs in the presence of 10 μM of Aβ42 for 12 hours, and MSC shows the results of culturing cerebral cortex-derived neurons in a culture medium without Aβ for 12 hours and then co-culturing the cerebral cortex-derived neurons with human UCB-derived MSCs for 12 hours. As shown in the first row of FIG. 6, tau protein was rapidly phosphorylated in the neurons but dephosphorylated by the co-culturing with the human UCB-derived MSCs (see Aβ42 and Aβ42/MSC of FIG. 6).

As shown in the second row of FIG. 6, DAPI staining shows that cerebral cortex-derived neurons that are not stained by the anti-phosphor-tau antibody in the first row of FIG. 6 are maintained. DAPI staining was performed using VECTASHIELD™ (VECTOR LABORATORIES), and a DAPI-containing mounting medium was added to a slide glass on which cells are deposited right before observing the cells using a microscope.

Example 7: Analysis of Differentiated Neurons Using Immunofluorescent Staining when Neurons Treated with Amyloid-Beta are Co-Cultured with Human UCB-Derived MSCs Neurons derived from the cerebral cortex and hippocampus were stained using antibodies specifically binding to microtubule-associated protein (MAP2) and Tubulin β III which are known as markers of differentiation of neurons.

An immunofluorescent staining was performed as follows. Neurons were fixed to wells of a 12-well plate using 4% paraformaldehyde for 20 minutes at room temperature, and washed four times with 0.1% BSA/PBS for 5 minutes each. Then, non-specific reaction was prevented by adding a solution containing 10% normal goat serum (NGS), 0.3% Triton X-100, and 0.1% BSA/PBS thereto and conducting reaction at room temperature for 30 to 45 minutes. A solution including a primary antibody, 10% NGS, and 0.1% BSA/PBS was added to the wells and reaction was conducted at 4° C. overnight. The resultant was washed three times with 0.1% BSA/PBS for 5 minutes each. A secondary antibody and a 0.1% BSA/PBS solution including a reagent binding to the secondary antibody was added thereto, and reaction was conducted for 4 minutes, and then the resultant was washed four times with 0.1% BSA/PBS for 5 minutes each. The primary antibody was prepared by diluting monoclonal anti-Tubulin β III antibody produced in mouse (Sigma) and rabbit anti-microtubule associated protein (MAP) 2 polyclonal antibody (Chemicon) in a buffer solution respectively at 1:500 and 1:200. The secondary antibody was prepared by respectively diluting biotinylated anti-mouse antibody and biotinylated anti-rabbit antibody, (Vector) in a buffer solution at 1:200. The reagent binding to the secondary antibody was prepared by diluting dichloro-triazinyl fluorescein (DTAF, Jackson immuno Research) in a buffer solution at 1:200.

In the neurons (cerebral and hippocampus-derived neurons) treated with Aβ42, neurites were cleaved and the shape of neurons was condensed due to toxicity. On the other hand, in neurons co-cultured with UCB-derived MSCs, neurites were maintained and maturation of the neurons were accelerated (FIGS. 7A, 7B, and 7C).

FIG. 7 illustrates neurons treated with Aβ42, co-cultured with UCB-derived MSCs, and stained using immunofluorescent staining using anti-Tubulin β III and anti-MAP2 and western blotting.

FIG. 7A shows cerebral cortex-derived neurons, FIG. 7B shows hippocampus-derived neurons. MAP2 and Tubulin β III respectively show the results of the stained immunofluorescent staining using anti-MAP2 and anti-Tubulin β III. Control shows the results of the control in which cerebral cortex-derived neurons or hippocampus-derived neurons were cultured in a serum-free Neurobasal™ culture medium without Aβ for 24 hours, Aβ42 shows the results of culturing cerebral cortex-derived neurons or hippocampus-derived neurons in a culture medium including 10 μM of Aβ for 24 hours, Aβ42/MSC shows the results of culturing cerebral cortex-derived neurons or hippocampus-derived neurons in a serum-free Neurobasal™ culture medium including 10 μM of Aβ for 12 hours and then co-culturing the cerebral cortex-derived neurons or hippocampus-derived neurons with human UCB-derived MSCs in the presence of 10 μM of Aβ42 for 12 hours, and MSC shows the results of culturing cerebral cortex-derived neurons or hippocampus-derived neurons in a culture medium without Aβ for 12 hours and then co-culturing the cerebral cortex-derived neurons or hippocampus-derived neurons with human UCB-derived MSCs for 12 hours.

FIG. 7C shows the results of co-culturing cerebral cortex-derived neurons treated with Aβ42 with UCB-derived MSCs and performing western blotting the co-cultured neurons using anti-MAP2 antibody. First, membranes of neurons were crushed using an ultra-sonicator in a Lysis buffer containing sodium dodecyl sulfate (SDS) to extract protein. The extracted protein was electrophoresed using a SDS-polyacrylamide gel to separate the protein according to the size. When the electrophoresis was terminated, the protein was transferred to a nitrocellulose membrane using electrical properties of the protein and reacted with the anti-MAP2 antibody (Millipore chem) diluted in PBS containing 3% skimmed milk. Then, an anti-rabbit antibody (Vector) conjugated to streptavidin-conjugated dichlorotriazinyl fluorescein (DTAF, Jackson immuno Research) was added thereto, and the resultant was treated with a substrate of enhanced chemiluminescence (ECL) solution, and then the resultant was developed using an X-ray film. In FIG. 7C, Control, Aβ, Aβ+MSC and MSC are the same as described above. In FIG. 7C, 200 indicates the molecular weight marker of 200 kDa.

Example 8: Induction of Expression of Neprilysin by Human UCB-Derived MSCs in Neurons and Microglial Cells Neprilysin (NEP) is known as a protein degrading Aβ42 in vivo with insulin degrading enzyme (IDE). In addition, it has been reported that knockout of NEP caused symptoms of Alzheimer's disease in mice. Neurons prepared in Examples 4 to 7 were collected and lysed to extract protein. The protein was separated using electrophoresis in a SDS-PAGE, and expression of the protein was measured by western blotting the separated protein using anti-neprilysin antibody. In addition, mRNA expression of NEP was measured using an NEP-specific primer by RT-PCR. In addition, the cultured cells were stained with anti-NEP antibody.

First, neurons were fixed to wells of a 12-well plate using 4% paraformaldehyde for 20 minutes at room temperature, and washed four times with 0.1% BSA/PBS for 5 minutes each. Then, non-specific reactions were prevented by adding a solution containing 10% normal goat serum (NGS), 0.3% Triton X-100, and 0.1% BSA/PBS thereto at room temperature for 30 to 45 minutes. A 10% NGS containing a primary antibody and 0.1% BSA/PBS were added to the wells and reaction was conducted at 4° C. overnight. The resultant was washed three times with 0.1% BSA/PBS for 5 minutes each. A secondary antibody and 0.1% BSA/PBS solution containing a reagent binding to the secondary antibody were added thereto, and reaction was conducted at room temperature for 40 minutes, and the resultant was washed four times with 0.1% BSA/PBS for 5 minutes each. Monoclonal anti-NEP antibody produced in mouse (Sigma) diluted in a buffer solution at 1:500 was used as the primary antibody. Biotinylated anti-mouse antibody (Vector) diluted in a buffer solution at 1:200 was used as the secondary antibody. Streptavidin-conjugated dichlorotriazinyl fluorescein (DTAF, Jackson Immuno Research) diluted in a buffer solution at 1:200 was used as the reagent binding to the secondary antibody.

Figure 8:
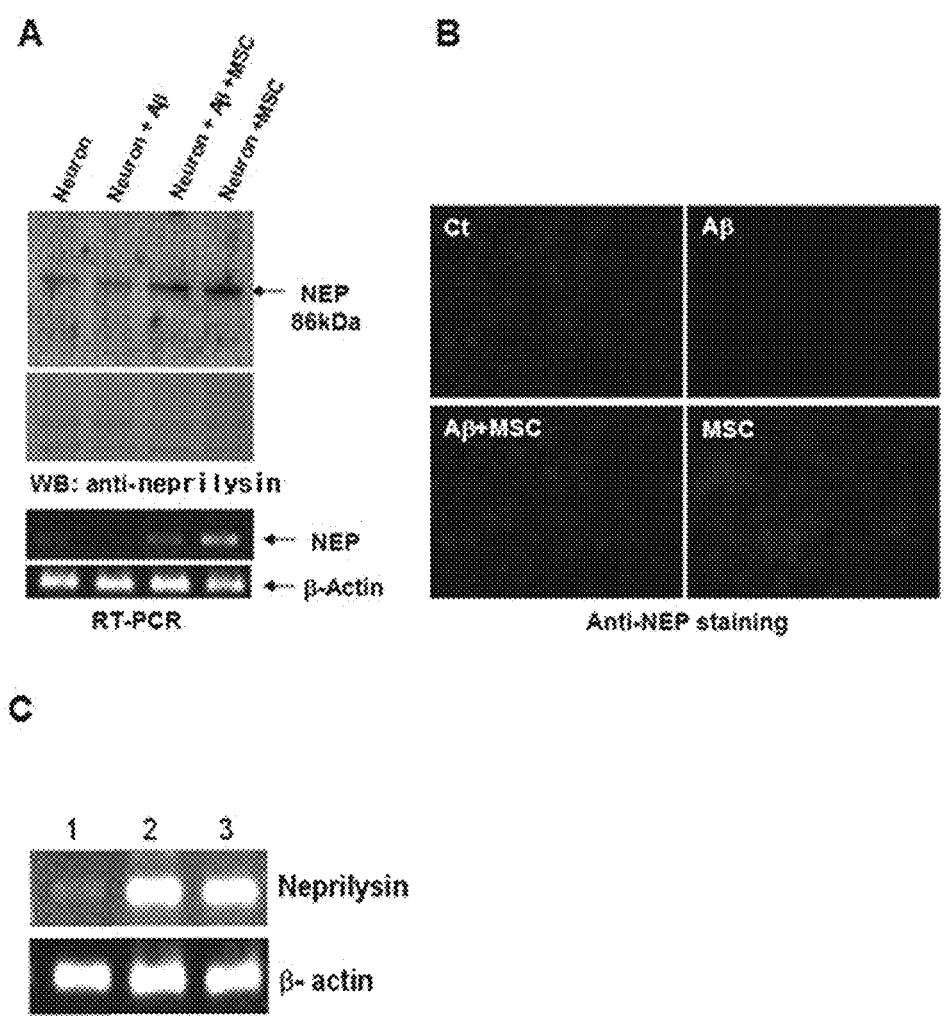
FIG. 8 illustrates expression of neprilysin in neurons treated with Aβ42 and co-cultured with bone marrow-derived MSCs or UCB-derived MSCs.

FIG. 8 illustrates expression of neprilysin in rat neurons treated with Aβ42 and co-cultured with human bone marrow-derived MSCs or human UCB-derived MSCs.

In FIG. 8A, the top shows a western blotting analysis of cultured rat cerebral cortex-derived neurons. Neuron shows the results of the control in which rat cerebral cortex-derived neurons were cultured in a serum-free Neurobasal™ culture medium without Aβ for 24 hours, Neuron+Aβ shows the results of culturing rat cerebral cortex-derived neurons in a culture medium including 10 μM of Aβ for 24 hours, the Neuron+Aβ+MSC shows the results of culturing rat cerebral cortex-derived neurons in a serum-free Neurobasal™ culture medium including 10 μM of Aβ for 12 hours and then co-culturing the rat cerebral cortex-derived neurons with human UCB-derived MSCs in the presence of 10 μM of Aβ for 12 hours, and Neuron+MSC shows the results of culturing rat cerebral cortex-derived neurons in a culture medium without Aβ for 12 hours and then co-culturing the rat cerebral cortex-derived neurons with human UCB-derived MSCs for 12 hours.

In FIG. 8A, the bottom shows a RT-PCR result using mRNA isolated from the cultured rat neurons as a template. PCR primers specific for NEP genes of a rat (SEQ ID NOS: 15 and 16) and PCR primers specific for β-actin genes (SEQ ID NOS: 17 and 18) were used. As a result of RT-PCR, amplified NEP gene (422 bp) and amplified β-actin gene (300 bp) were produced. Neuron, Neuron+Aβ, Neuron+Aβ-MSC, and Neuron+MSC are described above.

As shown in FIG. 8A, if rat neurons were treated with Aβ42, the expression of NEP was reduced. If the rat neurons treated with Aβ42 were co-cultured with human UCB-derived MSCs, the expression of NEP was increased in the protein and mRNA level. This indicates that human MSCs stimulate rat neurons to increase production of NEP and remove toxic Aβ42 protein.

In FIG. 8B, Ct, Aβ, Aβ+MSC, and MSC respectively correspond to Neuron, Neuron+Aβ, Neuron+Aβ+MSC, and Neuron+MSC.

The cells were stained according to the following process. First, neurons were fixed to wells of a 12-well plate using 4% paraformaldehyde for 20 minutes at room temperature, and washed four times with 0.1% BSA/PBS for 5 minutes each. Then, non-specific reactions were prevented by adding a solution containing 10% normal goat serum (NGS), 0.3% Triton X-100, and 0.1% BSA/PBS thereto at room temperature for 30 to 45 minutes. A 10% NGS containing a primary antibody and 0.1% BSA/PBS were added to the wells and reaction was conducted at 4° C. overnight. The resultant was washed three times with 0.1% BSA/PBS for 5 minutes each. A secondary antibody and a 0.1% BSA/PBS solution containing a reagent binding to the secondary antibody was added thereto, and reaction was conducted at room temperature for 40 minutes, and the resultant was washed four times with 0.1% BSA/PBS for 5 minutes each. Monoclonal anti-NEP antibody produced in mouse (Sigma) diluted in a buffer solution at 1:500 was used as the primary antibody. Biotinylated anti-mouse antibody (Vector) diluted in a buffer solution at 1:200 was used as the secondary antibody. Streptavidin-conjugated dichlorotriazinyl fluorescein (DTAF, Jackson immuno Research) diluted in a buffer solution at 1:200 was used as the reagent binding to the secondary antibody.

As shown in FIG. 8B, if the neurons were treated with Aβ42, the portion stained in red was considerably reduced, thereby indicating that the expression of NEP is reducing in the neurons. However, if the neurons were co-cultured with MSCs, the expression of the NEP was restored.

FIG. 8C shows the results of RT-PCR indicating that the expression of NEP in rat neurons was increased using bone marrow-derived MSCs (BM-MSCs).

The RT-PCR of NEP and β-actin were performed in the same condition using the same primers described with reference to FIG. 8A. In FIG. 8C, Lane 1 shows the results of the control in which rat cerebral cortex-derived neurons were cultured in a serum-free Neurobasal™ culture medium without Aβ for 24 hours, Lanes 2 and 3 show the results of culturing rat cerebral cortex-derived neurons in a culture medium without including Aβ for 12 hours, and then co-culturing the rat cerebral cortex-derived neurons with human bone marrow-derived MSCs (BM-MSC1 and BM-MSC2) for 12 hours. In this regard, BM-MSC1 and BM-MSC2 represents cells obtained from different donors. The results shown in FIG. 8C exhibit an increase of NEP expression in rat cerebral cortex-derived neurons when rat cerebral cortex-derived neurons are co-cultured with human BM-MSC at mRNA level. Further, according to the western blotting analysis and immunoblotting analysis, it was confirmed that when rat cerebral cortex-derived neurons are co-cultured with human BM-MSC, the NEP expression in the neurons are increased at a protein level.

The brain includes not only neurons but also microglial cells which are known as macrophage of the brain and remove toxic substances accumulated in the brain. The microglial cells remove Aβ in Alzheimer's disease. According to a recent report, a reduction in the expression of NEP in the microglial cells accelerates the progress of Alzheimer's disease. Thus, restoration of expression of NEP by human UCB cells was identified in neurons and microglial cells using an immunofluorescent staining (FIG. 9). FIG. 9 illustrates expression of neprilysin in neurons and microglial cells when neurons treated with Aβ42 are co-cultured with MSCs.

The first row of FIG. 9 shows cerebral cortex-derived neurons cultured in a serum-free Neurobasal™ culture medium including 10 μM of Aβ for 12 hours, then co-cultured with human UCB-derived MSCs in the presence of 10 μM of Aβ42 for 12 hours, and double stained using an antibody specifically binding to each of the markers of neurons MAP2 and NEP. The staining was performed in the same manner as in FIG. 8B, except that a rabbit anti-MAP2 antibody was used as a primary antibody, a biotinylated anti-rabbit antibody was used as a secondary antibody binding to the primary antibody, and streptavidin-conjugated dichlorotriazinyl fluorescein (DTAF, Jackson immuno Research) was used as a reagent binding to the secondary antibody for MAP2, and a monoclonal anti-NEP antibody produced in mouse (Sigma) was used as a primary antibody, a biotinylated anti-mouse antibody (Vector) was used as a secondary antibody, and streptavidin-conjugated dichlorotriazinyl fluorescein (DTAF, Jackson immuno Research) was used as a reagent binding to the secondary antibody for NEP. In the first row of FIG. 9, MAP2 and NEP show the neurons stained respectively using the anti-MAP2 antibody and the anti-NEP antibody, and MAP2+NEP shows an overlap image of the neurons stained respectively using the anti-MAP2 antibody and the anti-NEP antibody. DAPI shows the results stained using DAPI in the same manner as in the second row of FIG. 6.

Since both MAP2 and NEP show stained cells as shown in the first row of FIG. 9, it was identified that both of MAP2 and NEP are expressed in the neurons. In addition, as a result of the image overlap (MAP2+NEP), MAP2 and NEP are found in the same area, and thus it was identified that both of MAP2 and NEP are expressed. The neurons were stained by DAPI, and thus it was identified that the neurons are maintained in normal conditions.

The second row of FIG. 9 shows the results of the same experiments shown in the first row of FIG. 9, except that microglial cells were used instead of neurons and CD40 and NEP, as markers of microglial cells, were used, as markers of microglial cells instead of MAP2 and NEP. The staining of CD40 was performed using a goat anti-CD40 antibody as a primary antibody for CD40, biotin-conjugated anti-goat antibody as a secondary antibody binding to the primary antibody, and streptavidin-conjugated dichlorotriazinyl fluorescein (DTAF, Jackson immuno Research) diluted in a buffer solution at 1:200 as a reagent binding to the secondary antibody.

Since both CD40 and NEP show stained cells as shown in the second row of FIG. 9, it was identified that both of CD40 and NEP are expressed in the microglial cells. In addition, as a result of the image overlap (CD40+NEP), CD40 and NEP are found in the same area, and thus it was identified that both of MAP2 and NEP are expressed in the microglial cells. The microglial cells were stained by DAPI, and thus it was identified that the microglial cells are maintained in normal conditions.

According to the results of the first and second rows of FIG. 9, if the neurons and the microglial cells are co-cultured with UCB-derived MSCs, the expression of NEP was induced in the neurons and the microglial cells treated with Aβ.

Example 9: Identification of Protein Secreted by MSCs and Preventing Toxicity of Aβ42 and Verification of Effects of the Protein As a result of Examples 4 to 8, it was identified that toxicity of Aβ42 was inhibited in the neurons, if the neurons treated with Aβ42 were co-cultured with MSCs without direct contact therebetween. It can be predicted that the toxicity of Aβ42 can be inhibited by the interaction between substances secreted from the MSCs and the neurons.

In Example 9, substances that are secreted from the MSCs and inhibit toxicity of Aβ42 are detected and identified.

(1) Detecting MSC-Derived Substances Inhibiting Toxicity of Aβ42

First, cells were cultured in various conditions.

Culture group 1: Cerebral cortex-derived neurons were cultured in a serum-free Neurobasal™ culture medium without Aβ for 24 hours.

Culture group 2: Cerebral cortex-derived neurons were cultured in a serum-free Neurobasal™ culture medium including 10 μM of Aβ for 24 hours.

Culture group 3: Cerebral cortex-derived neurons were cultured in a serum-free Neurobasal™ culture medium including 10 μM of Aβ for 12 hours and then co-cultured with human UCB-derived MSCs in the presence of 10 μM of Aβ for 12 hours.

Culture group 4: Human UCB-derived MSCs were cultured in a serum-free Neurobasal™ culture medium including 10 μM of Aβ for 24 hours.

Culture groups 5 and 6: Human UCB-derived MSCs were cultured in a serum-free Neurobasal™ culture medium for 24 hours.

Then, the culture media of Culture groups 1 to 6 were collected, and cytokine and protein were assayed and compared with each other to detect cytokine or protein that are not expressed or rarely expressed when stem cells are only cultured but increasingly expressed when the stem cells and the neurons are co-cultured. The cytokine assay was performed using RayBio™ Human Cytokine Antibody Array I G series (RayBiotech, Inc), and the protein assay was performed using RayBio™ Human Cytokine Antibody Array I G series/Biotin Label Based Antibody Array I G series (RayBiotech, Inc). 54,504 proteins may be assayed using the two arrays.

By comparing data of the assays, protein that is not expressed or rarely expressed when stem cells are only cultured but increasingly expressed when the stem cells and the neurons are co-cultured was selected. As a result, the following 14 proteins were identified:

Activin A, platelet factor 4 (PF4), decorin, galectin 3, growth differentiation factor 15 (GDF15), glypican 3, membrane-type frizzled-related protein (MFRP), intercellular adhesion molecule 5 (ICAM5), insulin-like growth factor binding protein 7 (IGFBP7), platelet-derived growth factor-AA (PDGF-AA), secreted protein acidic and rich in cysteine (SPARCL1), thrombospondin-1 (TSP1), wnt-1 induced secreted protein 1 (WISP1), and progranulin (PGN).

It was estimated that the 14 proteins inhibit toxicity of neuron treated with Aβ and promote differentiation and maturation of the neurons.

(2) Identifying Activity of Detected 14 Proteins

Recombinant proteins of the detected 14 proteins were purchased from (R&D SYSTEMS). Then, cerebral cortex-derived neurons were treated with Aβ and cultured in a serum-free Neurobasal™ culture medium respectively containing 25 ng/ml of activin A, 25 ng/ml of PF4, 3 ng/ml of galectin 3, 100 ng/ml of decorin, 50 ng/ml of GDF15, 50 ng/ml of glypican 3, 50 ng/ml of MFRP, 50 ng/ml of ICAM5, 30 ng/ml of IGFBP7, 50 ng/ml of PDGF-AA, 50 ng/ml of SPARCL1, 50 ng/ml of TSP1, 50 ng/ml of WISP1 and 50 ng/ml of progranulin, for 24 hours. Then, the death of neuron was measured by fluorescent staining using a LIVE/DEAD™ viability/cytotoxicity assay kit (Sigma, L3224). The degree of cell death caused by Aβ was calculated based on the numbers of dead cells and live cells. The cell death was calculated using a ratio of the number of dead cells to the total number of cells.

FIG. 10 is a graph illustrating the percentage of dead neurons treated with Aβ42 and co-cultured with proteins secreted from MSCs. In FIG. 10, Cortex shows cerebral cortex-derived neurons cultured in a serum-free Neurobasal™ culture medium without Aβ42 for 24 hours, Cortex+Aβ shows cerebral cortex-derived neurons cultured in a serum-free Neurobasal™ culture medium including 10 μM of Aβ42 for 24 hours, Cortex+Aβ+MSC shows cerebral cortex-derived neurons cultured in a serum-free Neurobasal™ culture medium including 10 μM of Aβ42 for 12 hours and then co-cultured with UCB-derived MSCs in the presence of 10 μM of Aβ42 for 12 hours, and Cortex+MSC shows cerebral cortex-derived neurons cultured in a serum-free Neurobasal™ culture medium without Aβ42 for 12 hours and then co-cultured with UCB-derived MSCs for 12 hours. Aβ shows cerebral cortex-derived neurons cultured in a serum-free Neurobasal™ culture medium including Aβ42 and each of the 14 proteins having a concentration described above or 24 hours (In FIG. 10, $p<0.03$ and $p<0.01$ respectively indicate that error ranges of t-tests are respectively less than 3% and 1%).

As shown in FIG. 10, each of the 14 proteins inhibited the death of neuron caused by Aβ42. The degree of inhibiting the cell death decreases in the order of Cortex+Aβ+MSC, galectin 3, WISP1, and MFRP. This indicates that the co-culture with the MSCs, i.e., the combination of the 14 proteins has the greatest effect on inhibiting toxicity of Aβ.

In order to measure effects of protein on maturation of the neurons, the length of neurites in the cultured cells was measured. The neurons were cultured in the same conditions described with reference to FIG. 10. 100 cells were randomly selected from each culture group, and the length of neurites was measured using i-solution software (iMTechnology).

FIG. 11 is a graph illustrating the length of neurites of neurons cultured with Aβ42 and proteins secreted from MSCs. In FIG. 11, the culture groups are the same as those in FIG. 10, and the length of neurites are an average length. As shown in FIG. 11, each of the 14 proteins or a combination of the 14 proteins significantly increased the length of neurites compared to the neurons treated with Aβ42.

Example 10: Identification of Cytokine Secreted from MSCs and Inducing Expression of Neprilysin in Microglial Cells The co-culture system 100 described in Example 4 was used herein. Microglial cells (BV2) were cultured in the lower chamber 40, and UCB-derived MSCs (UCB-MSC) were cultured in the upper chamber 10. BV2 cells are immortalized cells prepared by infecting microglial cells of a mouse with v-raf/v-myc recombinant retrovirus and express traits of activated microglial cells. The co-culture was performed by culturing BV2 cells in a DMEM supplemented with 5% FBS in the lower chamber 40, adding UCB-derived MSCs cultured in a α-MEM supplemented with 5% FBS to the upper chamber 10, and replacing the culture medium with a serum-free DMEM. The cells were co-cultured in a serum-free DMEM for 24 hours. Then, the MSCs were collected from the upper chamber 10, and total RNA was obtained using a trizol reagent, and then RT-PCR was performed using the total RNA as a template. Primers that amplify genes of IL-4 (SEQ ID NOS: 22 and 23), IL-6 (SEQ ID NOS: 24 and 25), IL-8 (SEQ ID NOS: 26 and 27) and monocyte chemoattractant protein-1 (MCP-1, SEQ ID NOS: 28 and 29) were used. As a control group, β-actin was amplified using primers (SEQ ID NOS: 17 and 18). In the control group, UCB-derived MSCs (UCB-MSC) cultured in the same conditions described above, except that the UCB-derived MSCs were not co-cultured with microglial cells (BV2), were used.

Figure 12:
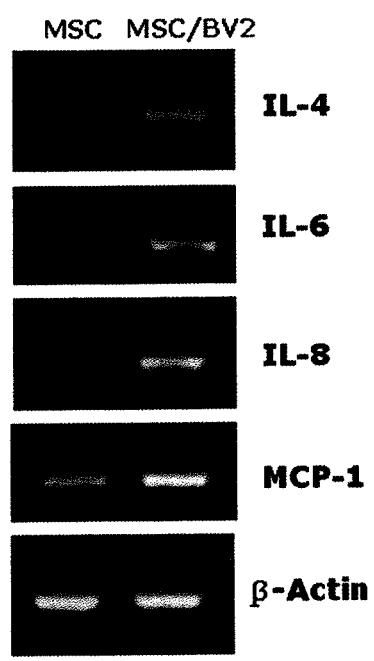
FIG. 12 shows the results of RT-PCR using the total RNA isolated from UCB-MSC as a template after co-culturing microglial cells with UCB-MSC.

FIG. 12 shows the results of RT-PCR using the total RNA isolated from UCB-MSC after co-culturing microglial cells with UCB-MSC as a template. As shown in FIG. 12, if the microglial cells and UCB-MSC are co-cultured, the expression of IL-4, IL-6, IL-8, and MCP-1 in UCB-MSC increased.

Microglial cells, BV2 cells, neurons, and SH-SY5Y cells (ATCC) were cultured respectively in the presence of IL-4, IL-6, IL-8 and MCP-1, and then BV2 cells and SH-SY5Y cells were collected. The collected cells were lysed and proteins were separated from the lysates according to the size, and the resultant was western blotted using an anti-NEP antibody. As a result, the expression of NEP increased with time in BV2 cells and SHY-5Y cells cultured in the presence of IL-4 when compared to in the absence of IL-4. The SH-SY5Y cells are thrice-cloned neurobastoma derived from SK-N-SH. The SH-SY5Y cells represent neuronal cells.

Figure 13:
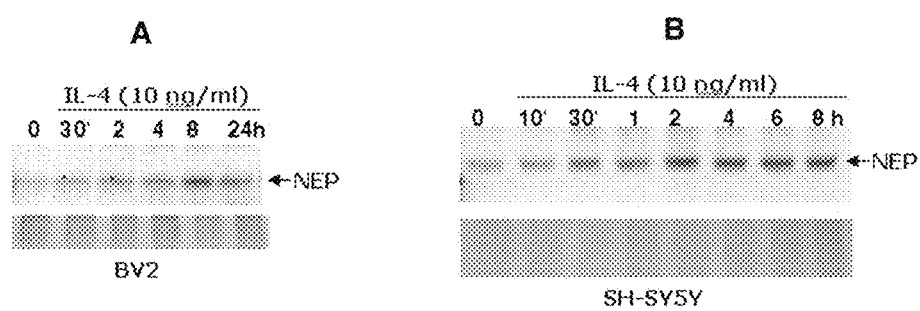
FIG. 13 shows the results of western blotting indicating the increase in the expression of NEP when neurons and microglial cells are cultured in the presence of IL-4.

FIG. 13 shows the results of western blotting indicating the increase in the expression of NEP when neurons and microglial cells are cultured in the presence of IL-4. FIG. 13A shows the results of western blotting of microglial cells (BV2 cells) cultured in DMEM including 10 ng/ml of IL-4 for 24 hours. FIG. 13B shows the results of western blotting of neurons (SH-SY5Y cells) cultured in α-MEM including 10 ng/ml of IL-4 for 24 hours.

Example 11: Reduction of Amyloid Protein Plaque by Administering UCB-Derived MSCs into Hippocampus and Cortex of a Mouse Transformed to have Alzheimer's Disease (Thioflavin-S Staining and Immuno-Blotting)

In order to improve effects of the treatment, PBS, $1 \times 10^4$ of UCB-derived MSCs in PBS, and 200 μg/kg (weight) of IL-4 (Peprotech) in PBS were administered into hippocampus of a 10 month-old mouse transformed to have Alzheimer's disease using a stereotactic frame. After 10 days, the mouse was killed, and brain tissue weres collected from hippocampus and cerebral cortex thereof. The obtained brain tissues were cut into slices and stained using thiosulfate (Sigma) to identify the amyloid-beta protein plaque. In order to identify the plaque, the brain tissue was reacted with a thioflavin solution (Sigma) dissolved in 50% ethanol for 5 minutes. After the reaction, the slices of the brain tissue was washed with 50% ethanol and water for 5 minutes. This slices were observed using a fluorescent microscope to identify amyloid protein plaque in the brain tissue.

Figure 14:
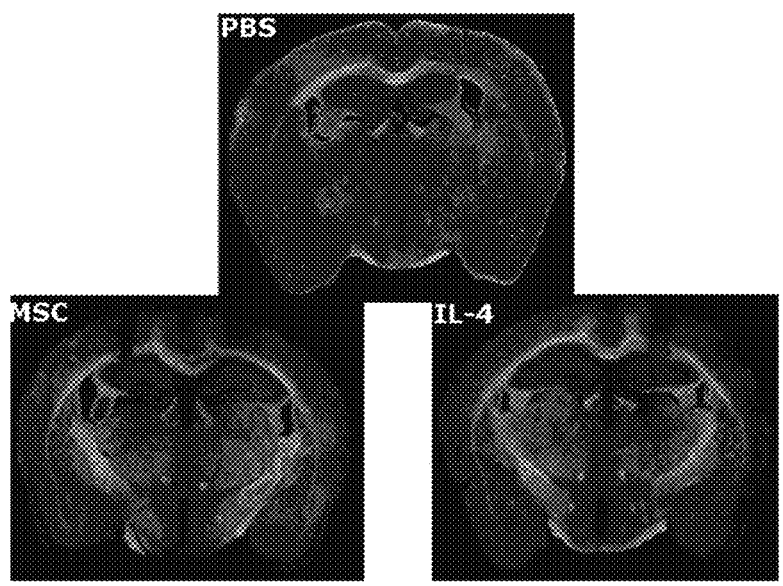
FIG. 14 shows images of Aβ protein plaque in a brain tissue including hippocampus and cerebral cortex stained using a Thio-S staining.

FIG. 14 shows images of amyloid-beta protein plaque in a brain tissue including hippocampus and cerebral cortex stained using a Thio-S staining. As shown in FIG. 14, the amyloid-beta protein plaque was significantly reduced in the culture groups into which UCB-derived MSCs and IL-4 were administered. In FIG. 14, PBS, MSC, and IL-4 respectively show the culture groups into which PBS, UCB-derived MSCs, and IL-4 were administered.

Figure 15:
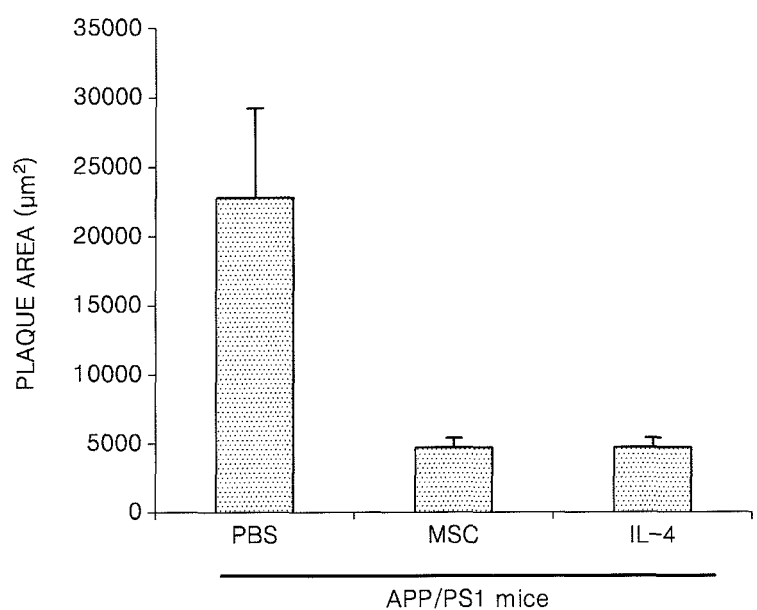
FIG. 15 is a graph illustrating the total area of Aβ plaque in the images of FIG. 14.

FIG. 15 is a graph illustrating the total area of amyloid-beta plaque in the images of FIG. 14. The area was measured using a Metamorpho software (Molecular devices). As shown in FIG. 15, the amyloid-beta plaque was significantly reduced in the culture groups into which MSCs and IL-4 were administered when compared to the control group.

Figure 16:
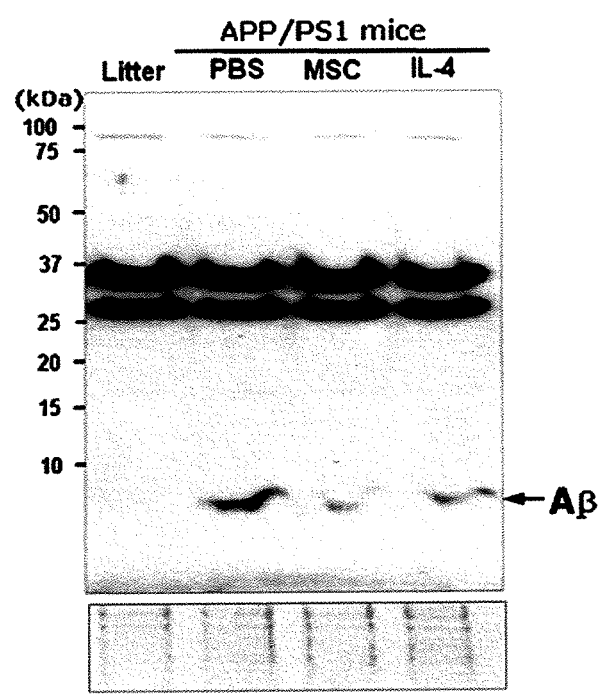
FIG. 16 shows the results of immunoblotting indicating the change of Aβ protein produced in the brain of a mouse used for an experiment.

FIG. 16 shows the results of immunoblotting indicating the change of amyloid-beta protein produced in the brain of a mouse used for an experiment. The graph of FIG. 16 was obtained according to the following process. First, protein was extracted from a brain tissue of a mouse including hippocampus and cerebral cortex and treated in the conditions described above using a sonicator (Branson). Then, the extract was separated according to the size using electrophoresis. The separated protein was transferred to a nitrocellulose membrane by a potential difference and an immuno-blotting was performed using an antibody capable of specifically detecting Aβ42. The proteins were stained using coomassie blue (bottom part). As shown in FIG. 16, the amount of Aβ42 protein was significantly reduced in the culture groups into which MSCs and IL-4 were administered when compared to the culture group into which PBS was administered. In FIG. 16, Litter indicates a littermate of a transformed mouse, and APP/PS1 mice indicates a mouse transformed to have Alzhemer's disease. In addition, PBS, MSC and IL-4 respectively show the culture groups into which PBS, MSC and IL-4 were administered.

Example 12: Effect of UCB-Derived MSCs and IL-4 on Expression of NEP (1) Expression of NEP in Brain Tissue of Normal Animal and Animal Transformed to have Alzheimer's Disease Brain tissues of normal mice and mice transformed to have Alzheimer's diseases respectively raised for 6, 9, 12 and 18 months were obtained, and protein was extracted in the same manner as in Example 11 and separated using electrophoresis. The separated protein was transferred to a nitrocellulose membrane and reacted with anti-NEP antibody (R&D systems) to analyze the expression of NEP.

Figure 17:
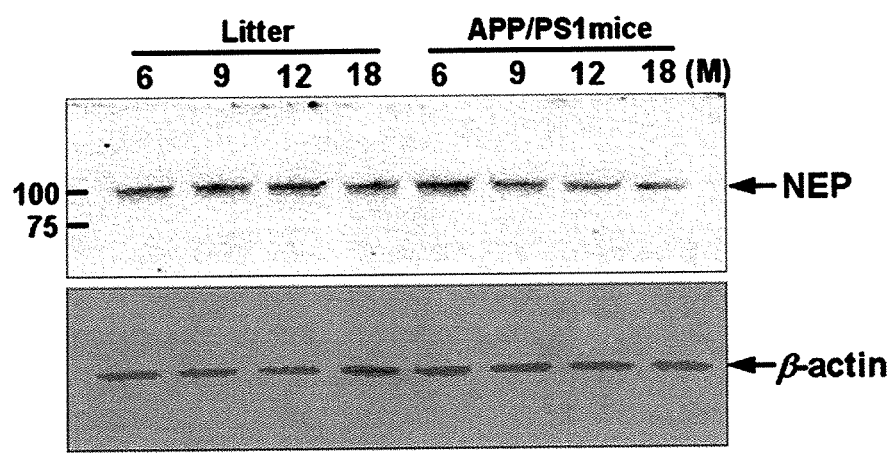
FIG. 17 shows the degree of expression of NEP in a brain tissue of a normal mouse and a mouse transformed to have Alzheimer's disease including hippocampus and cerebral cortex.

FIG. 17 shows the degree of expression of NEP in a brain tissue of a normal mouse and a mouse transformed to have Alzheimer's disease including hippocampus and cerebral cortex. As shown in FIG. 17, the expression of NEP was reduced in the brain tissue of the mouse transformed to have Alzheimer's disease. In FIG. 17, Litter and APP/PS1 mice are the same as those described with reference to FIG. 16. In addition, Lanes 6, 9, 12, and 18 respectively show the culture group cultured for 6, 9, 12, and 18 months (M: month).

Figure 18:
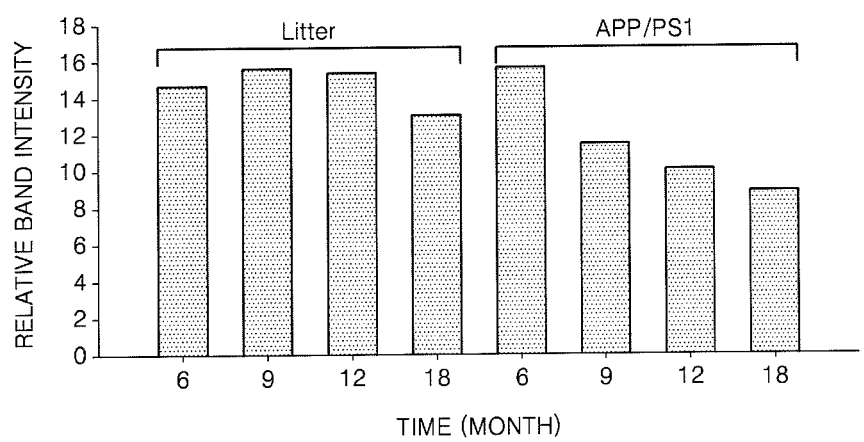
FIG. 18 is a graph illustrating band intensity of NEP of FIG. 17 measured using Quantity One software (Bio-RAD)

FIG. 18 is a graph illustrating band intensity of NEP of FIG. 17 measured using Quantity One software (Bio-RAD). The band intensity is a relative intensity. As shown in FIG. 18, the expression of NEP was reduced in the brain tissue of the mouse transformed to have Alzheimer's disease compared to that of the normal mouse.

(2) Effect of UCB-Derived MSCs and IL-4 on Expression of NEP

PBS, $1 \times 10^4$ of UCB-derived MSCs in PBS, and 200 μg/kg (weight) of IL-4 in PBS (Peprotech) were administered into hippocampus of a 10 month-old mouse transformed to have Alzheimer's disease. After 10 days, the mouse was killed, and brain tissue including hippocampus and cerebral cortex was collected. Proteins were extracted from each brain tissue and separated using electrophoresis to analyze the amount of expressed NEP using an immuno-blotting.

Figure 19:
FIG. 19 shows the degree of expression of NEP in a brain tissue of a mouse into which MSCs and IL-4 are administered and including hippocampus and cerebral cortex.
Figure 19:
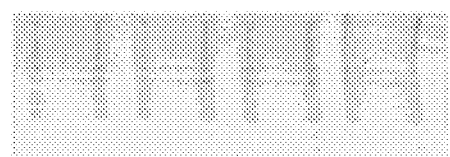

FIG. 19 shows the degree of expression of NEP in a brain tissue of a mouse into which MSCs and IL-4 are administered and including hippocampus and cerebral cortex. Coomassie blue was used for staining (bottom part). As shown in FIG. 19, the expression of NEP was reduced in the culture group into which PBS was administered when compared to the normal mouse as shown in operation (1) described above, and the expression of NEP in the culture group into which UCB-derived MSCs and IL-4 were administered was similar to that of the normal mouse.

Example 13: Effect of UCB-Derived MSCs and IL-4 on Expression of NEP in Microglial Cells In Example 8, it was identified that NEP was overexpressed in neurons and microglial cells when the neurons and microglial cells are respectively co-cultured with MSCs.

In Example 13, this effect was identified in an animal model. Brain hippocampus tissue of the culture groups into which PBS, UCB-derived MSCs, and IL-4 were administered described in Example 12 were stained in the same manner as shown in FIG. 8B. The anti-NEP antibody and the anti-CD40 antibody, as a marker of microglial cells (Santacruz Biotechnology) were used and the results were merged. In the anti-NEP antibody staining, the secondary antibody and the reagent binding to the secondary antibody are the same as those described in Example 8. Also, in the anti-CD40 antibody staining, the secondary antibody and the reagent binding to the secondary antibody are the same as those described in Example 8.

Figure 20:
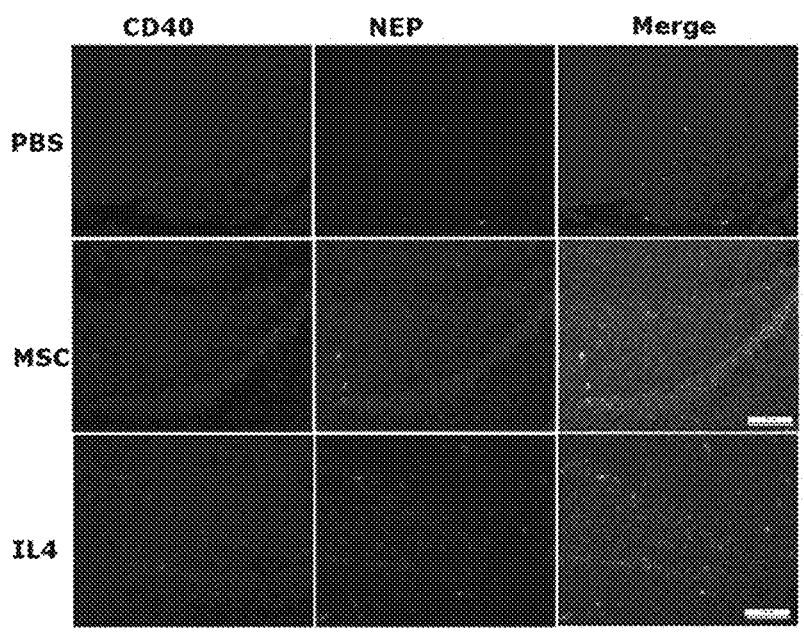
FIG. 20 shows the expression of NEP in microglial cells of a mouse into which UCB-derived MSCs and IL-4 are administered.

FIG. 20 shows the expression of NEP in microglial cells of a mouse into which UCB-derived MSCs and IL-4 are administered. As shown in FIG. 20, when UCB-derived MSCs and IL-4 are administered into an animal model, overexpression of NEP was induced in microglial cells.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method of treating a neural disease selected from the group consisting of Alzheimer's disease and Parkinson's disease, the method comprising administering directly a pharmaceutical composition comprising, as an active ingredient, a culture solution of umbilical cord blood-derived mesenchymal stem cells (UCB-MSCs) into the brain of a subject in need of treating the neural disease,
wherein the culture solution of UCB-MSCs is obtained by a process comprising co-culturing UCB-MSCs with amyloid-beta-treated neurons without direct contact between the UCB-MSCs and the amyloid beta-treated neurons, said UCB-MSCs and said amyloid beta-treated neurons being separated from each other by a porous membrane.

2. The method of claim 1, wherein the neural disease is a disease caused by at least one selected from the group consisting of formation of amyloid-beta plaque in neural tissues, phosphorylation of tau protein in neurons, damage to neurites, reduction in expression of neprilysin in neurons, and any combination thereof.

3. The method of claim 2, wherein the neural disease is formation of amyloid-beta plaque in neural tissues.

4. The method of claim 2, wherein the neural disease is phosphorylation of tau protein in neurons.

5. The method of claim 2, wherein the neural diseases is reduction in expression of neprilysin in neurons.

6. The method of claim 1, wherein the pharmaceutical composition is administered into hippocampus of the subject.

7. The method of claim 1, wherein the culture solution of UCB-MSC comprises activin A, platelet factor 4 (PF4), decorin, galectin 3, growth differentiation factor 15 (GDF15), glypican 3, membrane-type frizzled-related protein (MFRP), intercellular adhesion molecule 5 (ICAM5), insulin-like growth factor binding protein 7 (IGFBP7), platelet-derived growth factor-AA (PDGF-AA), secreted protein acidic and rich in cysteine (SPARCL1), thrombospondin-1 (TSP1), wnt-1 induced secreted protein 1 (WISP1), and progranulin (PGN).

8. A method of treating a neural disease selected from the group consisting of Alzheimer's disease and Parkinson's disease, the method comprising administering directly a pharmaceutical composition comprising, as an active ingredient, co-cultured umbilical cord blood-derived mesenchymal stem cells (UCB-MSCs) into brain parenchyma or ventricle of a subject in need of treating the neural disease,
wherein the co-cultured UCB-MSCs are obtained by a process comprising co-culturing UCB-MSCs with amyloid-beta-treated neurons without direct contact between the UCB-MSCs and the amyloid beta-treated neurons and the UCB-MSCs and the amyloid beta-treated neurons are separated by a porous membrane.

9. The method of claim 8, wherein the pharmaceutical composition comprising the co-cultured UCB-MSCs contains actavin A, platelet factor 4, decorin, galectin 3, growth differentiation factor 15, glypican 3, membrane-type frizzled-related protein, intercellular adhesion molecule 5, insulin-like growth factor binding protein 7, platelet-derived growth factor-AA, secreted protein acidic and rich in cysteine, thrombospondin-1, wnt-1 induced secreted protein 1, and progranulin.

10. A method for reducing amyloid-beta plaques in neural tissues of a subject, comprising administering directly a pharmaceutical composition comprising, as an active ingredient, co-cultured umbilical cord blood-derived mesenchymal stem cells (UCB-MSCs) into brain parenchyma or ventricle of the subject,
wherein the co-cultured UCB-MSCs are obtained by a process comprising co-culturing UCB-MSCs with amyloid-beta-treated neurons without direct contact between the UCB-MSCs and the amyloid beta-treated neurons and the UCB-MSCs and the amyloid beta-treated neurons are separated by a porous membrane.

11. The method of claim 10, wherein the pharmaceutical composition comprising the co-cultured UCB-MSCs contains actavin A, platelet factor 4, decorin, galectin 3, growth differentiation factor 15, glypican 3, membrane-type frizzled-related protein, intercellular adhesion molecule 5, insulin-like growth factor binding protein 7, platelet-derived growth factor-AA, secreted protein acidic and rich in cysteine, thrombospondin-1, wnt-1 induced secreted protein 1, and progranulin.

12. A method for increasing an expression of neprilysin in neural tissues of a subject, comprising administering directly a pharmaceutical composition comprising, as an active ingredient, co-cultured umbilical cord blood-derived mesenchymal stem cells (UCB-MSCs) into brain parenchyma or ventricle of the subject,
wherein the co-cultured UCB-MSCs are obtained by a process comprising co-culturing UCB-MSCs with amyloid-beta-treated neurons without direct contact between the UCB-MSCs and the amyloid beta-treated neurons and the UCB-MSCs and the amyloid beta-treated neurons are separated by a porous membrane.

13. The method of claim 12, wherein the pharmaceutical composition comprising the co-cultured UCB-MSCs contains actavin A, platelet factor 4, decorin, galectin 3, growth differentiation factor 15, glypican 3, membrane-type frizzled-related protein, intercellular adhesion molecule 5, insulin-like growth factor binding protein 7, platelet-derived growth factor-AA, secreted protein acidic and rich in cysteine, thrombospondin-1, wnt-1 induced secreted protein 1, and progranulin.

* * * * *